(12) United States Patent  
Kono et al.

(10) Patent No.: US 7,984,649 B2  
(45) Date of Patent: Jul. 26, 2011

(54) PANEL INSPECTION APPARATUS AND INSPECTION METHOD

(75) Inventors: Ichiro Kono, Tochigi (JP); Kenzo Takeda, Tochigi (JP); Shin Yoshida, Tochigi (JP)

(73) Assignee: Honda Motor Co., Ltd., Tokyo (JP)

( * ) Notice: Subject to any disclaimer, the term of this patent is extended or adjusted under 35 U.S.C. 154(b) by 447 days.

(21) Appl. No.: 12/262,537

(22) Filed: Oct. 31, 2008

(65) Prior Publication Data

US 2009/0114018 A1    May 7, 2009

(30) Foreign Application Priority Data

Nov. 1, 2007   (JP) .................................. 2007-284919

(51) Int. Cl.  
*G01N 29/12* (2006.01)
(52) U.S. Cl. ................. 73/579; 73/584; 73/588; 73/602
(58) Field of Classification Search .................... 73/579, 73/584, 588, 602  
See application file for complete search history.

(56) References Cited

U.S. PATENT DOCUMENTS

| 5,874,676 | A | * | 2/1999 | Maki, Jr. ......................... 73/579 |
| 6,031,917 | A | * | 2/2000 | Mathur ....................... 381/71.11 |
| 6,138,996 | A | * | 10/2000 | Hayashi et al. ................ 267/136 |
| 7,346,177 | B2 | * | 3/2008 | Willems .......................... 381/98 |

FOREIGN PATENT DOCUMENTS

| JP | 09-171008 | 6/1997 |
| JP | 2007-147512 | 6/2007 |

* cited by examiner

*Primary Examiner* — Jacques M Saint Surin  
(74) *Attorney, Agent, or Firm* — Rankin, Hill & Clark LLP

(57) ABSTRACT

A panel inspection apparatus includes a resonant frequency extracting unit for extracting a plurality of resonant frequencies of a panel, a resonant frequency selecting unit for selecting a combination of resonant frequencies consisting of two resonant frequencies A and B with different vibration propagation paths among the extracted plurality of resonant frequencies, a non-defective range generating unit for generating a non-defective range on a coordinate system in which resonant frequencies A and B are taken on coordinate axes by statistically processing a set of the resonant frequencies A and B selected for each of a plurality of non-defective panels determined as non-defective in advance, and a panel quality determining unit for determining whether the quality of the panel to be inspected is good based on comparison between resonant frequencies A and B selected for the panel to be inspected and the non-defective range generated by the non-defective range generating unit.

5 Claims, 23 Drawing Sheets

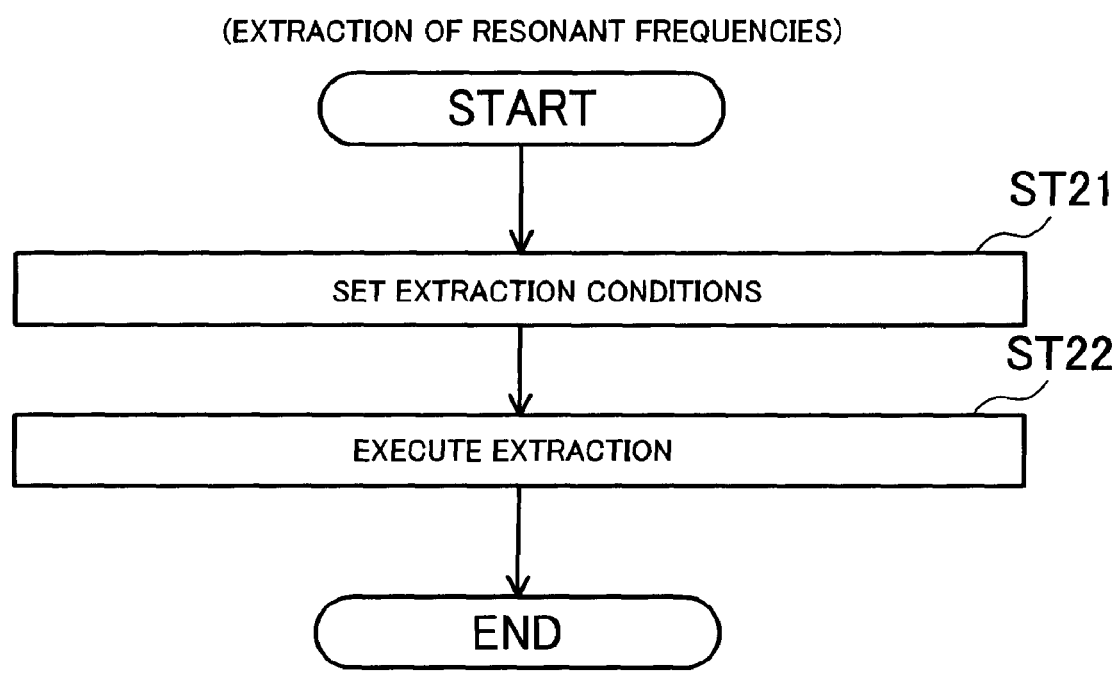

FIG.11

| | NON-DEFECTIVE PANEL 1 | NON-DEFECTIVE PANEL 2 | NON-DEFECTIVE PANEL 3 | NON-DEFECTIVE PANEL 4 | NON-DEFECTIVE PANEL 5 | ... |
|---|---|---|---|---|---|---|
| RESONANT FREQUENCY A | 550.2 | 550.5 | 550.1 | 550.2 | 550.1 | ... |
| RESONANT FREQUENCY B | 652.4 | 652.6 | 652.3 | 652.2 | 652.5 | ... |
| RESONANT FREQUENCY C | 901.1 | 901.5 | 900.9 | 901.2 | 901.9 | ... |
| RESONANT FREQUENCY D | 1102.5 | 1102.2 | 1101.8 | 1102.7 | 1102.4 | ... |
| ... | ... | ... | ... | ... | ... | |

| | NON-DEFECTIVE PANEL 1 | NON-DEFECTIVE PANEL 2 | NON-DEFECTIVE PANEL 3 | NON-DEFECTIVE PANEL 4 | NON-DEFECTIVE PANEL 5 | ... |
|---|---|---|---|---|---|---|
| RESONANT FREQUENCY A | 2705.1 | 2705.3 | 2704.8 | 2703.9 | 2705.5 | ... |
| RESONANT FREQUENCY B | 752.4 | 752.0 | 751.6 | 752.5 | 752.1 | ... |

| | NON-DEFECTIVE PANEL 1 | NON-DEFECTIVE PANEL 2 | NON-DEFECTIVE PANEL 3 | NON-DEFECTIVE PANEL 4 | NON-DEFECTIVE PANEL 5 | ... |
|---|---|---|---|---|---|---|
| RESONANT FREQUENCY B | 752.4 | 752.0 | 751.6 | 752.5 | 752.1 | ... |
| RESONANT FREQUENCY C | 2522.2 | 2523.0 | 2522.5 | 2520.9 | 2521.8 | ... |

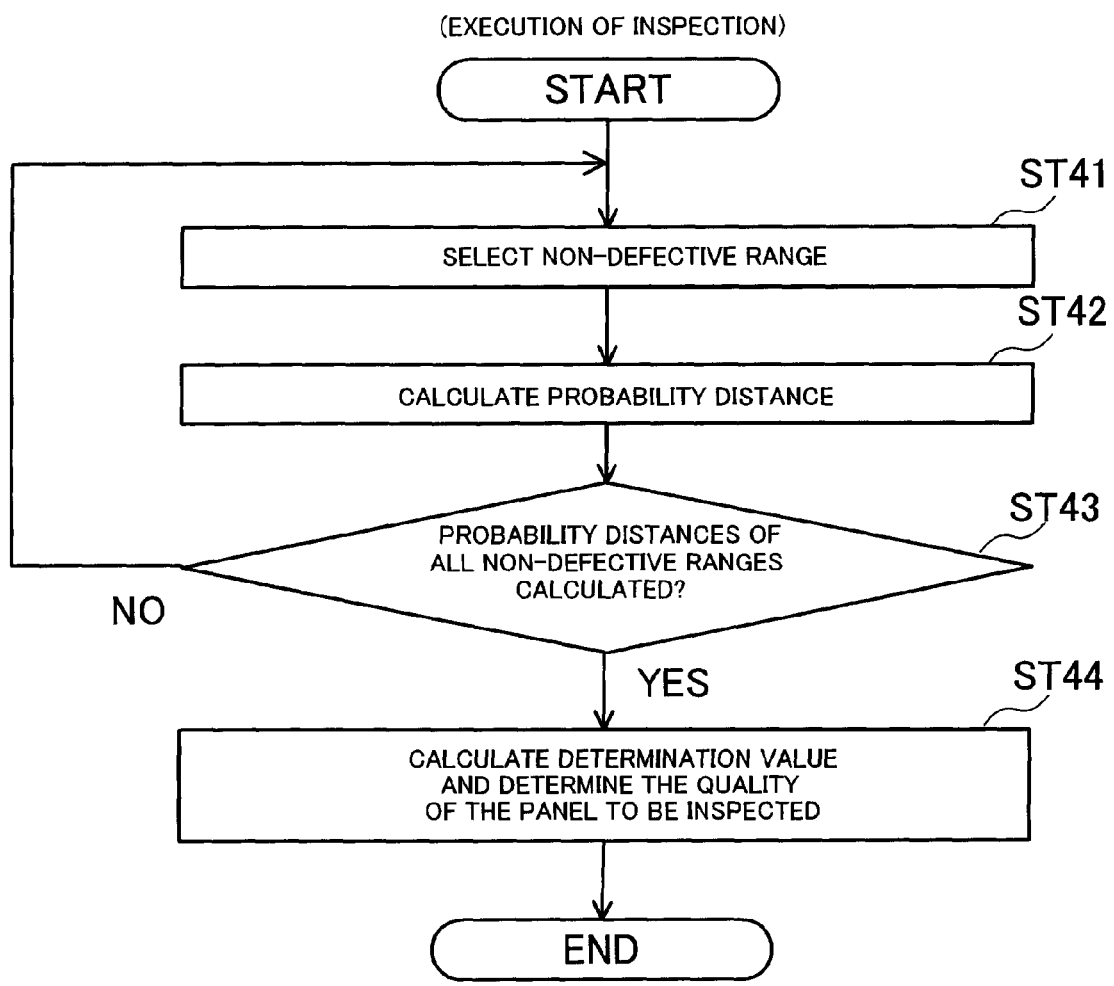

PANEL INSPECTION APPARATUS AND INSPECTION METHOD

BACKGROUND OF THE INVENTION

1. Field of the Invention

The present invention relates to a panel inspection apparatus and inspection method. Specifically, the present invention relates to a panel inspection apparatus and inspection method for measuring resonant frequencies of a panel formed as a press-formed product and determining whether the quality of the panel is good based on the resonant frequencies.

2. Background Art

When a panel is formed by press-forming a plate material, the panel may be constricted or cracked. Such constrictions and cracks easily occur in particular at portions such as flange and corner portions at which distortion is concentrated during press-forming. However, at some portions, the constriction and crack occur unexpectedly, so that it is difficult to estimate the occurring locations. Therefore, the inspection of constrictions and cracks must be performed extensively for the entire formed item, and may take time.

Conventionally, an inspection apparatus which can perform an inspection of constrictions and cracks of a panel in a short time has been proposed. As such an inspection apparatus, for example, in JP-A-09-171008 and JP-A-2007-147512, inspection apparatuses which vibrate a panel, detect the vibrations of the panel, and based on a frequency characteristics unique to the panel extracted from the detected vibrations, determine whether the quality of the panel is good, are shown.

FIG. 24 is a histogram showing distributions of plate thicknesses of a plurality of plate materials included in one standard.

In FIG. 24, the horizontal axis indicates the plate thickness of the plate material, and the vertical axis indicates frequency. As shown in this figure, plate materials to be used as materials of press-formed products have variation in plate thickness although they are included in the same standard.

However, if the plate materials to be used as materials have such variation in plate thickness, it cannot be distinguished whether a change in frequency characteristics of a panel is caused by the presence of a constriction and a crack or caused by variation in plate thickness of plate materials. In the above-described Patent documents 1 and 2, such variation in plate thickness is not considered, and therefore, determination on the quality of the panel may be different from actuality.

SUMMARY OF THE INVENTION

One or more embodiments of the invention provide a panel inspection apparatus and a panel inspection method for determining whether the quality of a panel is good based on the frequency characteristics of the panel, and in which variation in plate thickness of plate materials before being press-formed is considered.

In accordance with one or more embodiments of the invention, a panel inspection apparatus (for example, a panel inspection apparatus 1 described later) determines whether a quality of a panel to be inspected is good based on resonant frequencies obtained by vibrating panels determined as non-defective in advance. The panel inspection apparatus is provided with, a vibrator (for example, a vibrator 20 described later) which vibrates the panel, a vibration detector (for example, a vibration sensor 30 described later) which detects vibrations of the panel, and a resonant frequency extracting unit (for example, a control device 40 described later and means for executing Steps ST3 and ST6 of FIG. 2, etc.) for extracting a plurality of resonant frequencies of the panel by using the vibrator and the vibration detector. The panel inspection apparatus also including a resonant frequency selecting unit (for example, the control device 40 described later and means for executing Step ST32 of FIG. 12, etc.) which selects one or more combinations of resonant frequencies consisting of two or more resonant frequencies with different vibration propagation paths among the plurality of resonant frequencies extracted by the resonant frequency extracting unit, a non-defective range generating unit (for example, the control device 40 described later and means for executing Step ST33 of FIG. 12, etc.) for generating non-defective ranges related to a plurality of non-defective panels determined as non-defective in advance on coordinate systems in which the resonant frequencies are taken on coordinate axes by executing the resonant frequency extracting unit and the resonant frequency selecting unit and statistically processing a set of the combinations of resonant frequencies selected for each non-defective panel, and a panel quality determining unit (for example, the control device 40 described later and means for executing Step ST7 of FIG. 2, etc.) for determining whether the quality of the panel to be inspected is good based on comparison between combinations of resonance frequencies selected for the panel to be inspected and the non-defective ranges generated by the non-defective range generating unit upon executing the resonant frequency extracting unit and the resonant frequency selecting unit for the panel to be inspected.

According to the embodiment of the invention, from a plurality of non-defective panels determined as non-defective in advance, combinations of resonant frequencies unique to the respective non-defective panels are selected, and a set of these combinations of resonant frequencies are statistically processed to generate non-defective ranges on coordinate systems in which the resonant frequencies are taken on coordinate axes. Next, from a panel to be inspected, combinations of resonant frequencies unique to the panel to be inspected are selected, and the combinations of resonant frequencies and the generated non-defective ranges are compared to determine whether the quality of the panel is good.

Particularly, as the combination of resonant frequencies, by selecting two or more resonant frequencies with different vibration propagation paths, a non-defective range having an extent in which variation in plate thickness of plate materials to be used as materials is considered can be generated. By determining whether the quality of the panel to be inspected is good based on such a non-defective range, the quality of the panel can be inspected by considering the variation in plate thickness of materials.

By detecting the vibrations of the panel by a vibration detector while vibrating the panel by a vibrator, the quality of the panel can be inspected in a short time. Accordingly, for example, a panel inspection apparatus can be incorporated in a panel production line.

The panel quality determining unit may use only non-defective ranges which have a positive correlation between resonant frequencies among the non-defective ranges generated by the non-defective range generating unit for determining whether the quality of the panel to be inspected is good.

Herein, the resonant frequencies of the panel are in proportion to the plate thickness of a plate material used as a material of the panel. Therefore, the resonant frequencies of the panel have a positive correlation.

By using only non-defective ranges in which resonant frequencies have a positive correlation for determining whether the quality of the panel to be inspected is good, erroneous determination on the quality of the panel can be prevented.

The panel inspection apparatus may be incorporated in a press-formed panel production line consisting of a plurality of processes (for example, a production line 100 described later).

By incorporating the panel inspection apparatus in a press-formed panel production line, the time cycles of the panel production and the panel inspection can be shortened.

In accordance with one or more embodiments of the invention, a panel inspection method, for determining whether the quality of a panel to be inspected is good based on resonant frequencies obtained by vibrating panels determined as non-defective in advance, includes a resonant frequency extracting step at which a panel is vibrated and the vibrations are detected, and a plurality of resonant frequencies of the panel are extracted, and a resonant frequency selecting step at which one or more combinations of resonant frequencies consisting of two or more resonant frequencies with different vibration propagation paths are selected among the plurality of resonant frequencies extracted at the resonant frequency extracting step. The panel inspection method further including a non-defective range generating step at which, for a plurality of non-defective panels determined as non-defective in advance, the inspection step is executed, and a set of the combinations of the resonant frequencies selected for the non-defective panels is statistically processed to generate non-defective ranges generated on coordinate systems in which the resonant frequencies are taken on coordinate axes;, and a panel quality determining step at which, for the panel to be inspected, the inspection step is executed, combinations of resonant frequencies selected for the panel to be inspected and the non-defective ranges generated by the non-defective range generating unit are compared, and based on this comparison, it is determined whether the quality of the panel to be inspected is good.

When determining whether the quality of the panel to be inspected is good, only non-defective ranges having a positive correlation between resonant frequencies among the non-defective ranges may be used for determining whether the quality of the panel to be inspected is good.

The panel inspection method brings about the same effect as that of the panel inspection apparatus.

According to the panel inspection apparatus, by selecting two or more resonant frequencies with different vibration propagation paths as a combination of resonant frequencies, a non-defective range having an extent in which variation in plate thickness of plate materials used as materials is considered can be generated. By determining whether the quality of the panel to be inspected is good based on such non-defective ranges, the quality of the panel can be inspected while considering the variation in plate thickness of the materials. By detecting vibrations of the panel by a vibration detector while vibrating the panel by a vibrator, the quality of the panel can be inspected in a short time. Accordingly, for example, the panel inspection apparatus can be incorporated in a panel production line.

Other aspects and advantages of the invention will be apparent from the following description, the drawings and the claims.

BRIEF DESCRIPTION OF THE DRAWINGS

FIG. 9 is a flowchart showing steps for extracting resonant frequencies;

FIG. 11 is a diagram showing an example of a plurality of resonant frequencies extracted commonly from a plurality of non-defective panels;

FIG. 19 is a flowchart showing steps for executing the inspection of a panel to be inspected;

DETAILED DESCRIPTION OF THE EXEMPLARY EMBODIMENTS

Hereinafter, an exemplary embodiment of the present invention will be described with reference to drawings.

Figure 1:
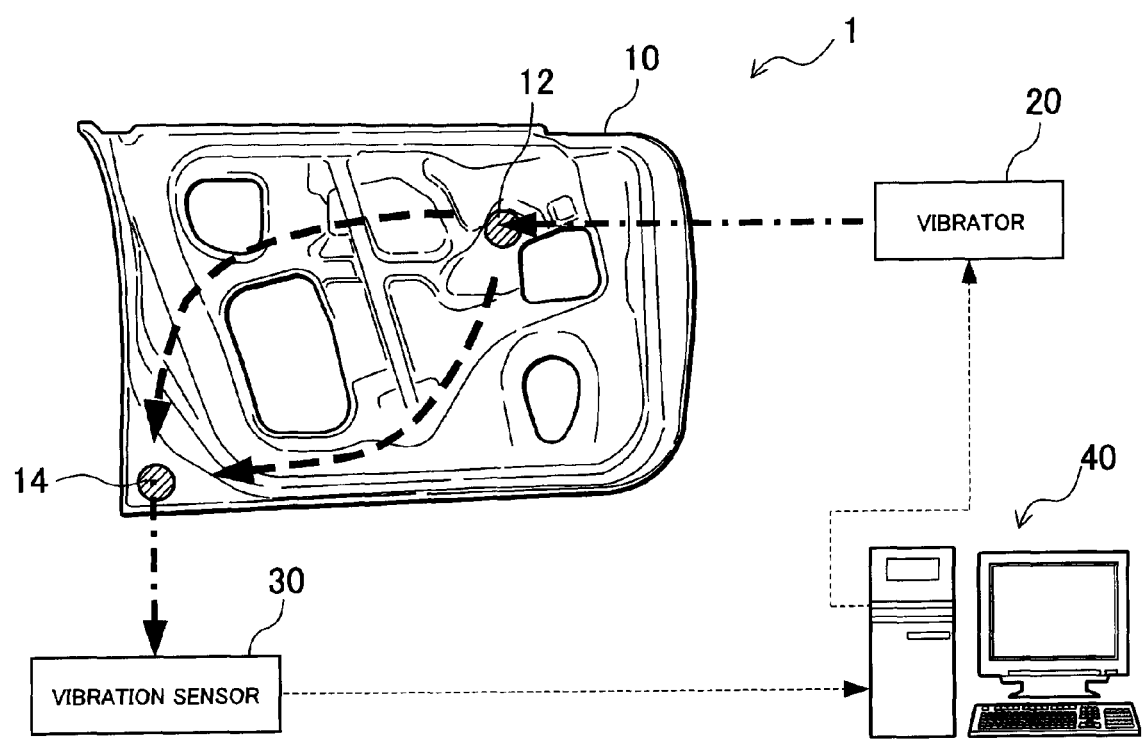
FIG. 1 is a schematic view showing a construction of a panel inspection apparatus of an exemplary embodiment of the present invention.

FIG. 1 is a general view showing a construction of a panel inspection apparatus 1 of the exemplary embodiment of the present invention.

The panel inspection apparatus 1 includes a vibrator 20 which vibrates a press-formed panel 10, a vibration sensor 30 as a vibration detector which detects vibrations of the panel 10, and a control device 40 which controls the vibrator 20 and the vibration sensor 30.

In the panel inspection apparatus 1, while a vibration position 12 provided on one end portion of the panel 10 is vibrated by the vibrator 20, the vibrations are detected by the vibration sensor 30 at a detection position 14 provided on the other end portion of the panel 10, and by processing the detected vibrations by the control device 40, it is determined whether the quality of the panel 10 is good.

As the vibrator 20, an electromagnetic (electrodynamic) vibrator capable of stably applying vibrations with large amplitude is used. The vibrator 20 generates vibrations corresponding to a voltage waveform generated by the control device 40. An output shaft of the vibrator 20 is in contact with the vibration position 12 of the panel 10, and vibrates the panel 10 according to the input voltage waveform. The vibrator 20 has a magnet which adsorbs the panel 10 to the output shaft for reliably transmitting the vibrations of the output shaft to the panel 10.

The vibration sensor 30 detects vibrations of the panel 10 as a response to vibration applied from the vibrator 20 from the detection position 14. In detail, as the vibration sensor 30, a noncontact velocimeter such as a laser Doppler velocimeter is used. The vibration sensor 30 is connected to the control device 40, and outputs a detection signal to the control device 40.

The control device 40 includes an input device for inputting various data and instructions by an operator, an arithmetic device which executes various arithmetic processings in response to inputs from the input device, and a display device which displays arithmetic processing results as images. The arithmetic device of the control device 40 generates a voltage waveform to be output to the vibrator 20 and executes panel inspection processing described later in response to a detection signal input from the vibration sensor 30 to determine whether the quality of the panel 10 is good.

Next, steps for inspecting a panel by the panel inspection apparatus 1 will be described.

Figure 2:
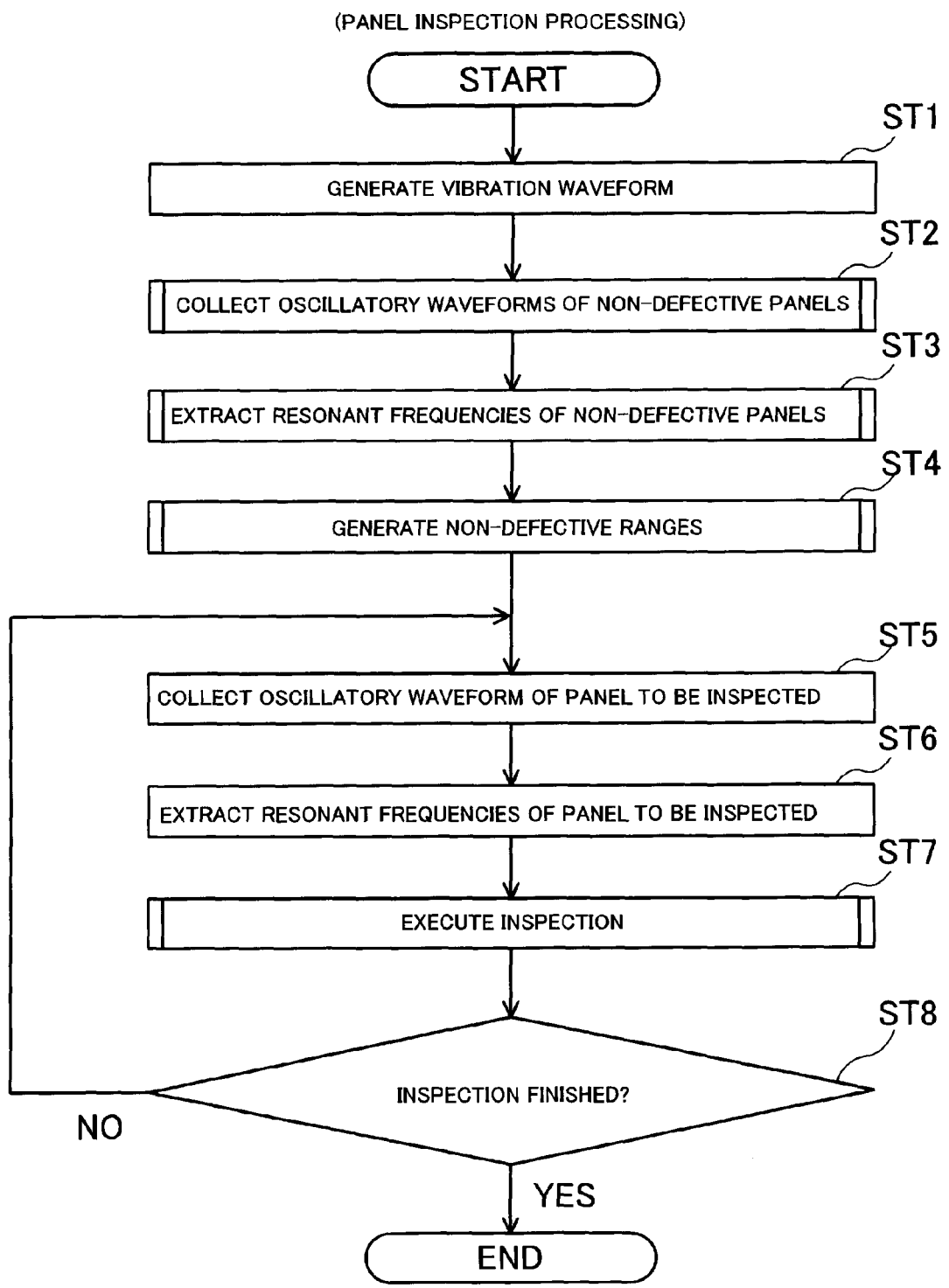
FIG. 2 is a flowchart showing steps of panel inspection processing of the panel inspection apparatus of the embodiment.

FIG. 2 is a flowchart showing the steps of the panel inspection processing.

First, at Step ST1, a vibration waveform to be applied to the panel is generated (see FIG. 3 and FIG. 4 described later).

At Step ST2, a plurality of panels determined as non-defective in advance are prepared and vibrated by the vibrator, and oscillatory waveforms as responses are collected (see FIG. 5 to FIG. 8 described later).

At Step ST3, from the oscillatory waveforms collected at Step ST2, a plurality of resonant frequencies of each non-defective panel are extracted (see FIG. 9 to FIG. 11 described later).

At Step ST4, based on the plurality of resonant frequencies of each panel extracted at Step ST3, non-defective ranges are generated (see FIG. 12 to FIG. 17 described later).

At Step ST5, a panel to be inspected is vibrated by the vibrator, and an oscillatory waveform as a response is collected.

At Step ST6, from the oscillatory waveform collected at Step ST5, a plurality of resonant frequencies of the panel to be inspected are extracted.

At Step ST7, the plurality of resonant frequencies of the panel to be inspected extracted at Step ST6 are compared with the non-defective ranges generated at Step ST4 to determine whether the quality of the panel to be inspected is good (see FIG. 19 and FIG. 20 described later).

At Step ST8, it is determined whether the inspection has been finished. When the result of this determination is "YES,"
the panel inspection processing is ended, and when it is "NO," the panel to be inspected is replaced and the process shifts to Step ST5.

Hereinafter, the processings of Steps ST1 to ST8 will be described in order.

First, generation of a vibration waveform (Step ST1 in FIG. 2), that is, generation of a voltage waveform to be input into the vibrator will be described with reference to FIG. 3 and FIG. 4.

Figure 3:
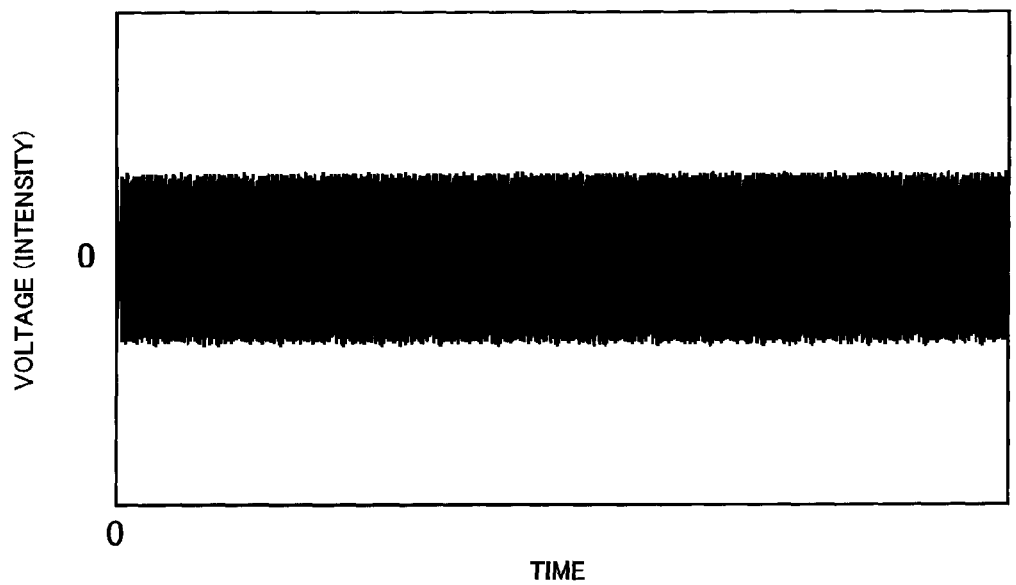
FIG. 3 is a diagram showing an example of a vibration waveform.

FIG. 3 is a diagram showing an example of a vibration waveform. In FIG. 3, the horizontal axis indicates the time, and the vertical axis indicates the voltage. The vibration waveform must be an oscillatory waveform including all the plurality of resonant frequency components of the panel to be described in detail later. Therefore, in the exemplary embodiment, the vibration waveform is generated by superimposing a plurality of sine waves with different frequencies.

Figure 4:
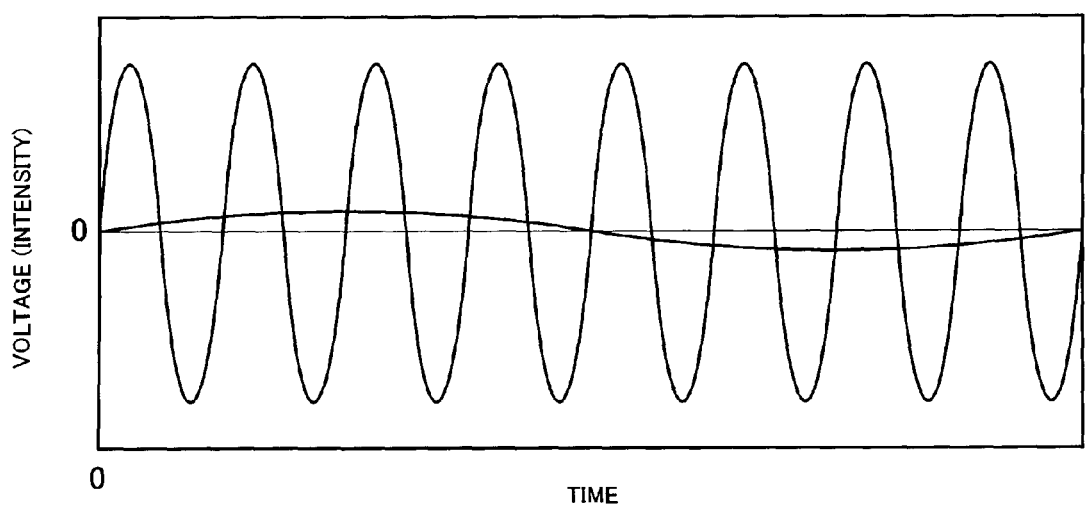
FIG. 4 is a diagram showing two of a plurality of sine waves composing the vibration waveform.

FIG. 4 is a diagram showing two of the plurality of sine waves composing the vibration waveform.

The vibration waveform is composed by superimposing sine waves with different frequencies as shown in FIG. 4 by shifting the phases of their peaks from each other. In the exemplary embodiment, as the vibration waveform, for example, a waveform including 9210 frequency components each 0.38 Hz between 500 Hz and 4000 Hz is used. The amplitude of the vibration waveform is generated according to a maximum voltage value which is allowed to be input into the vibrator.

Due to the characteristics of the vibrator, the driving capability of the vibrator becomes lower as the frequency becomes higher. Therefore, when superimposing the sine waves with different frequencies, by increasing the intensities of the frequency components according to this frequency characteristic of the vibrator, even comparatively high resonant frequencies can be detected by the vibration sensor.

Next, the steps for collecting the oscillatory waveforms of non-defective panels (Step ST2 in FIG. 2) will be described with reference to FIG. 5 to FIG. 8.

Figure 5:
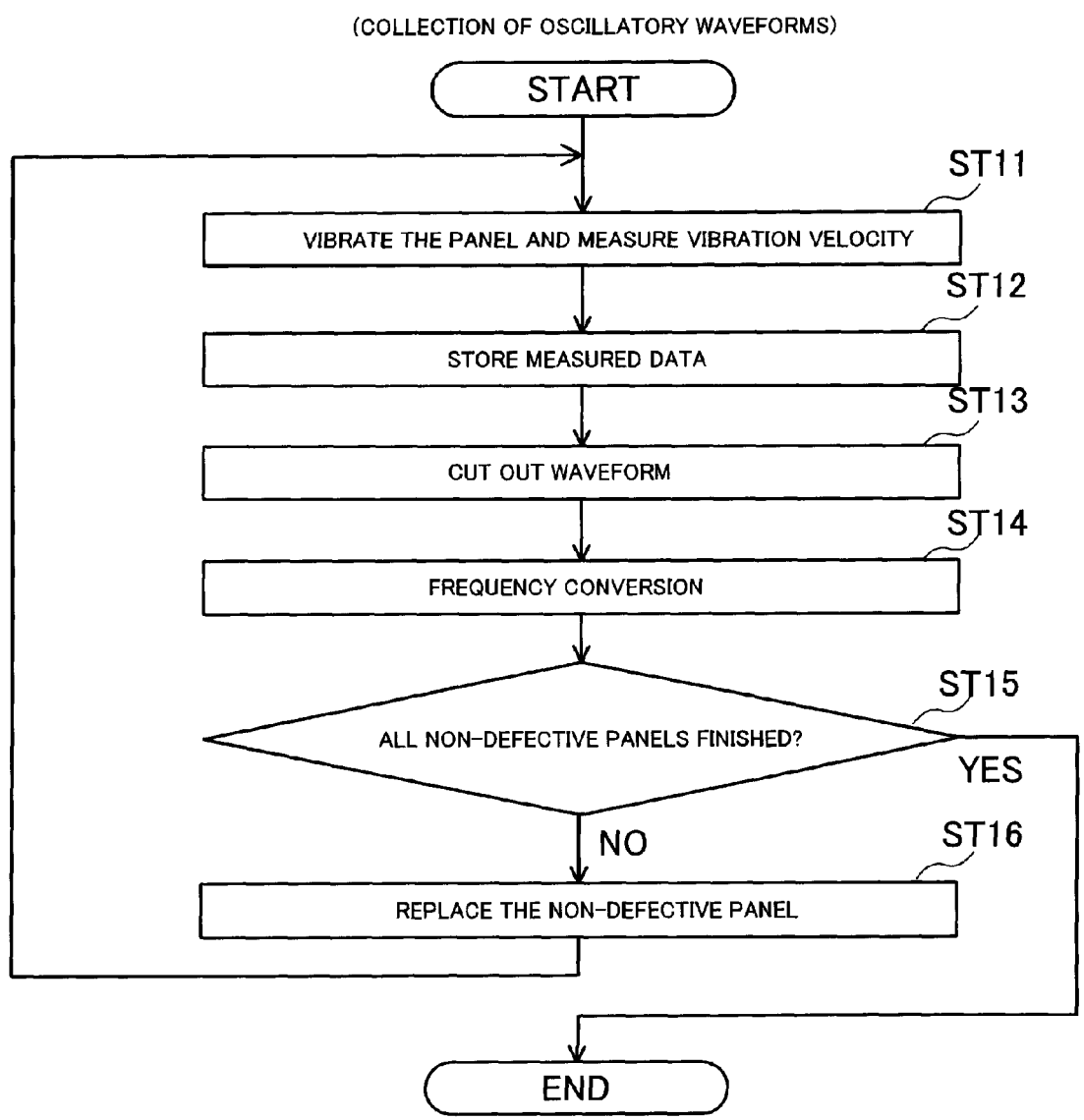
FIG. 5 is a flowchart showing steps for collecting oscillatory waveforms.

FIG. 5 is a flowchart showing the steps for collecting oscillatory waveforms.

Figure 6:
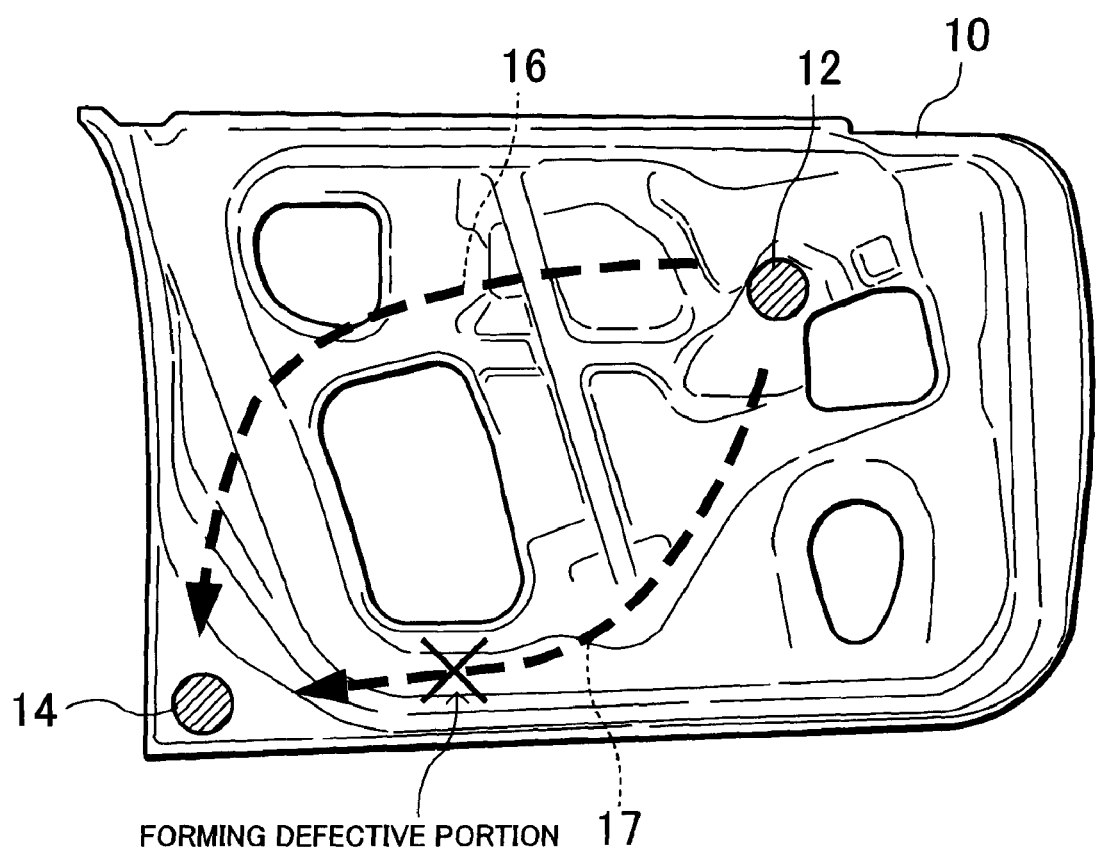
FIG. 6 is a view showing a construction of the panel.

FIG. 6 is a view showing a construction of the panel 10.

First, at Step ST11, for a predetermined time, while vibrating the panel 10 by the vibrator, the vibration velocity of the panel 10 is measured by the vibration sensor, and then the process shifts to Step ST12. In detail, at this step, based on the vibration waveform generated at the above-described Step ST1, while vibrating the vibration position 12 by the vibrator, the vibration velocity of the panel 10 at the detection position 14 is measured by the vibration sensor. Herein, in detail, the time for vibrating the panel and detecting the vibrations is set to, for example, 1 second.

At Step ST12, the waveform of the measured vibration velocity is stored as measurement data, and the process shifts to Step ST13.

At Step ST13, only a portion to be used for the inspection in the measured vibration velocity waveform is cut out, and the process shifts to Step ST14.

Figure 7:
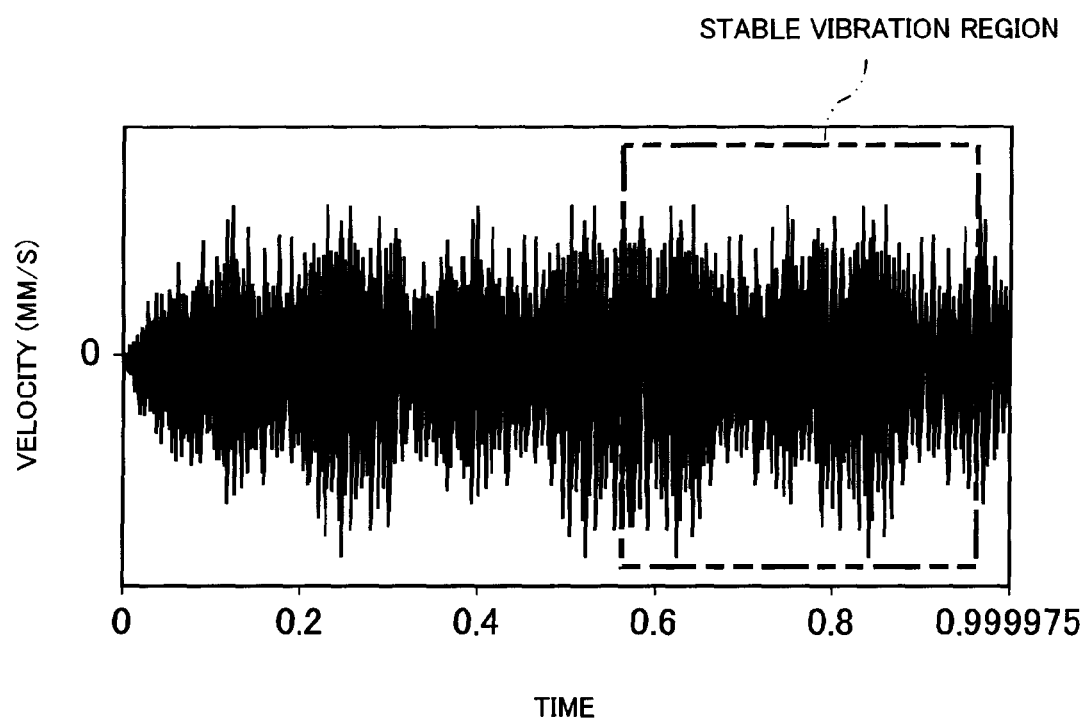
FIG. 7 is a diagram showing an example of a vibration velocity waveform.

FIG. 7 is a diagram showing an example of the measured vibration velocity waveform, and at the time 0, vibrating was performed and measurement of the vibration velocity was started, and thereafter, the vibration velocity was measured for about 1 second. Immediately after starting vibrating, the vibrations of the panel are not stable, and are not suitable for extraction of resonant frequencies described in detail later. Therefore, at this step, as shown by the alternate long and short double-dashed line in FIG. 7, only the portion in a steady state where the oscillatory waveform is stable is cut out.

At Step ST14, by frequency-converting (spectrum-converting) the vibration velocity waveform cut out at Step ST13, the vibrations of the panel are decomposed into frequency components.

Figure 8:
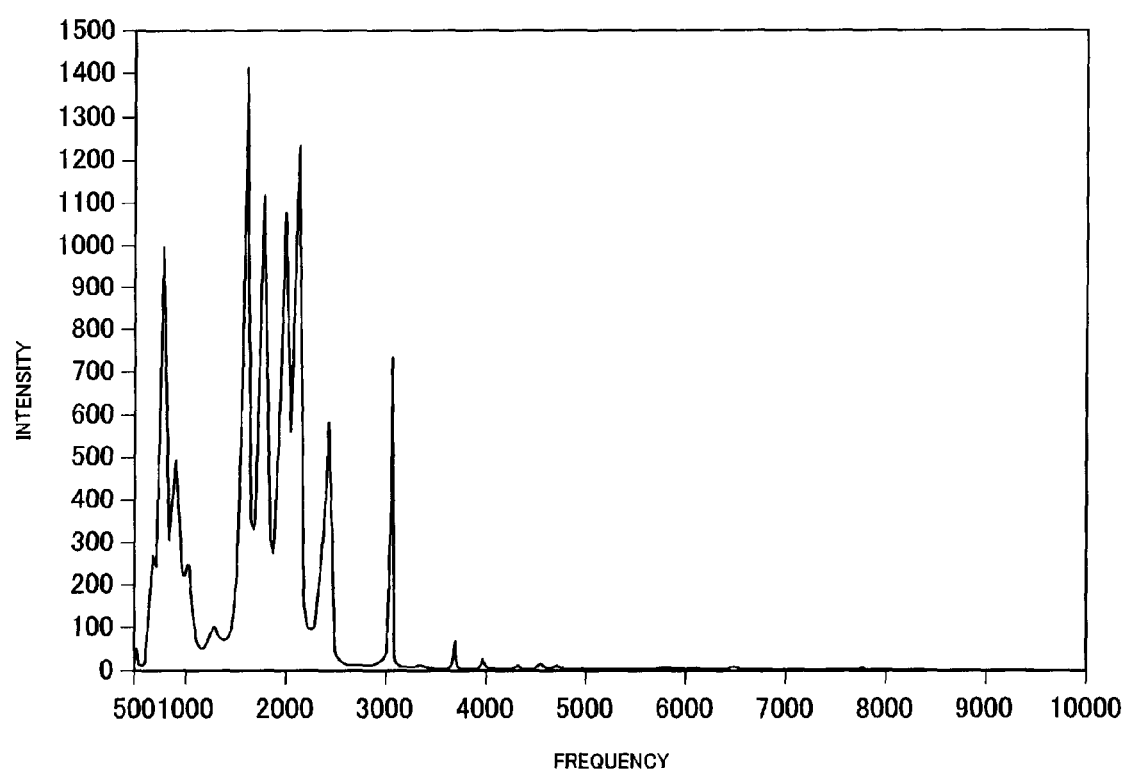
FIG. 8 is a diagram showing an example of a waveform of frequency components.

FIG. 8 is a diagram showing an example of a waveform of frequency components. In FIG. 8, the horizontal axis indicates the frequency, and the vertical axis indicates the intensity of the vibration of each frequency.

As shown in FIG. 8, when the vibration velocity waveform of the panel are decomposed by frequency, steep peaks are detected at some frequencies. These peaks show that a resonance phenomenon occurred by vibrating the panel. In other words, the frequency vibrations with these peaks show that the vibrations caused by vibrating the panel and a reflected wave of the vibrations superimposed and caused amplification. The value of the frequency with these peaks, that is, the resonant frequency values and the values of these peaks depend on the shape and plate thickness, etc., of the panel, and are unique to the panel.

The resonance phenomenon is generally caused by vibrations with a plurality of frequencies. As shown in FIG. 6, there are a plurality of paths on which the vibrations propagate as indicated by the arrows 16 and 17 of the dashed lines. Therefore, one panel has resonant frequencies different between the vibration propagation paths.

At this step, as a method for decomposing the vibration velocity waveform into frequency components, the maximum entropy method is used. However, without limiting to this, methods such as the fast Fourier transform, etc., may also be used.

Returning to FIG. 5, at Step ST15, it is determined whether oscillatory waveforms of all non-defective panels have been collected. When the result of this determination is "YES," collection of the oscillatory waveforms of the non-defective panels is ended, and when it is "NO," the non-defective panel is replaced (ST16) and the process shifts to Step ST11.

Next, steps for extracting resonant frequencies of the non-defective panels (Step ST3 in FIG. 2) will be described with reference to FIG. 9 to FIG. 11.

FIG. 9 is a flowchart showing steps for extracting the resonant frequencies.

At Step ST21, extraction conditions are set, and the process shifts to Step ST22. At this step, from the waveforms of frequency components collected from the respective non-defective panels at the above-described Step ST14, resonant frequencies common for all non-defective panels are extracted.

Figure 10A:
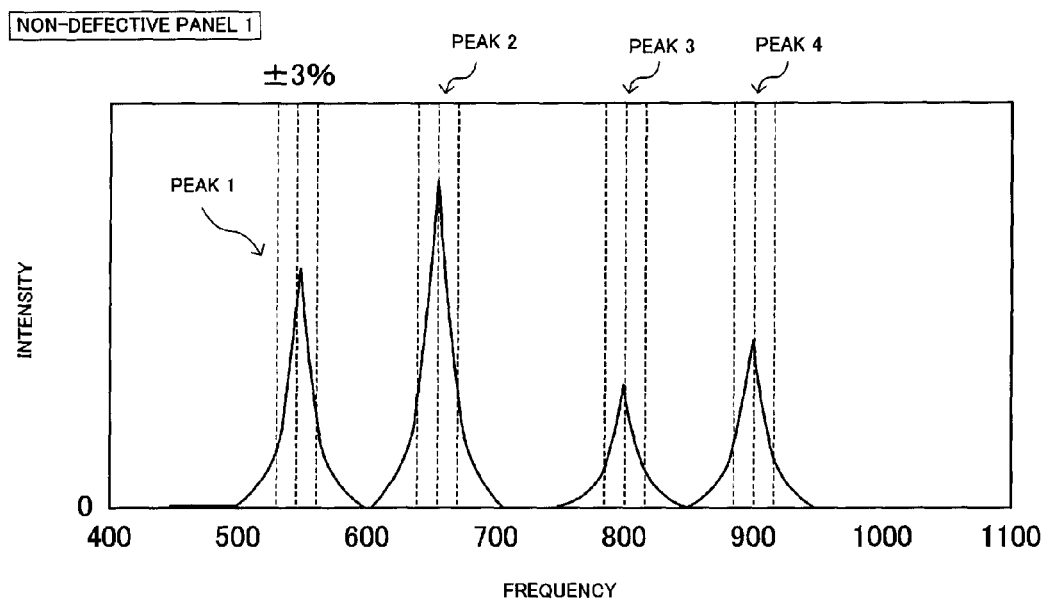
FIGS. 10($a$) and 10($b$) are diagrams showing examples of waveforms of frequency components.
Figure 10B:
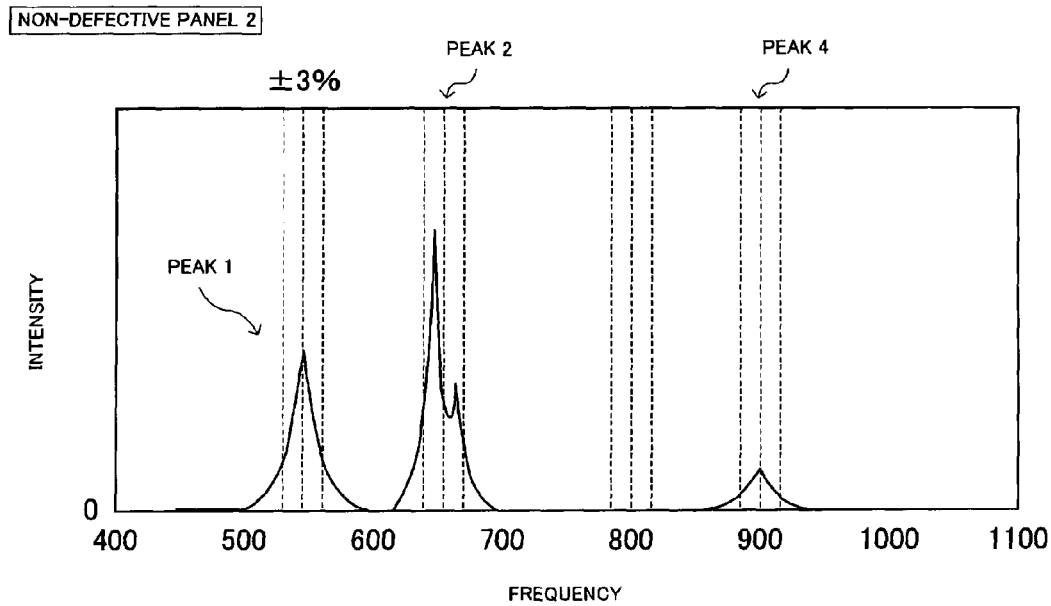

FIGS. 10(a) and 10(b) are diagrams showing examples of the waveforms of frequency components obtained at the above-described Step ST14. In detail, FIG. 10(a) shows a waveform of frequency components of the non-defective panel 1, and FIG. 10(b) shows a waveform of frequency components of the non-defective panel 2.

As shown in FIGS. 10(a) and 10(b), in the waveform of frequency components of the non-defective panel 1, between the frequencies 400 Hz and 1100 Hz, a peak 1 around 550 Hz, a peak 2 around 650 Hz, a peak 3 around 800 Hz, and a peak 4 around 900 Hz are observed. On the other hand, in the non-defective panel 2, peaks corresponding to the peaks 1, 2, and 4 of the non-defective panel 1 are observed. However, a peak corresponding to the peak 3 of the non-defective panel 1 is not observed. The values of the peaks of these non-defective panels 1 and 2 are different from each other. Thus, even in panels determined as non-defective, the waveform of frequency components is different among the panels according to influences of the difference in plate thickness of the plate materials as materials and measurement noise.

Therefore, at this step, conditions for extracting a peak which is common for all non-defective panels and can be stably observed as a resonant frequency are set.

In detail, a panel as a reference is selected, and extraction conditions for extracting frequencies which are ±3 percent of the central frequencies of peaks of this reference panel and can be detected with stable intensities from all non-defective panels are set. Accordingly, for example, the peak 3 in FIG. 10(a) is regarded as not detectable with a stable intensity and excluded from resonant frequencies to be extracted.

At Step ST22, under the set extraction conditions, resonant frequencies are extracted. Accordingly, as shown in FIG. 11, from each of the plurality of non-defective panels 1, 2, 3, 4, 5 . . . , a plurality of resonant frequencies A, B, C, D . . . can be extracted.

Next, steps for generating non-defective ranges (Step ST4 in FIG. 2) will be described with reference to FIG. 12 to FIG. 17(b).

Figure 12:
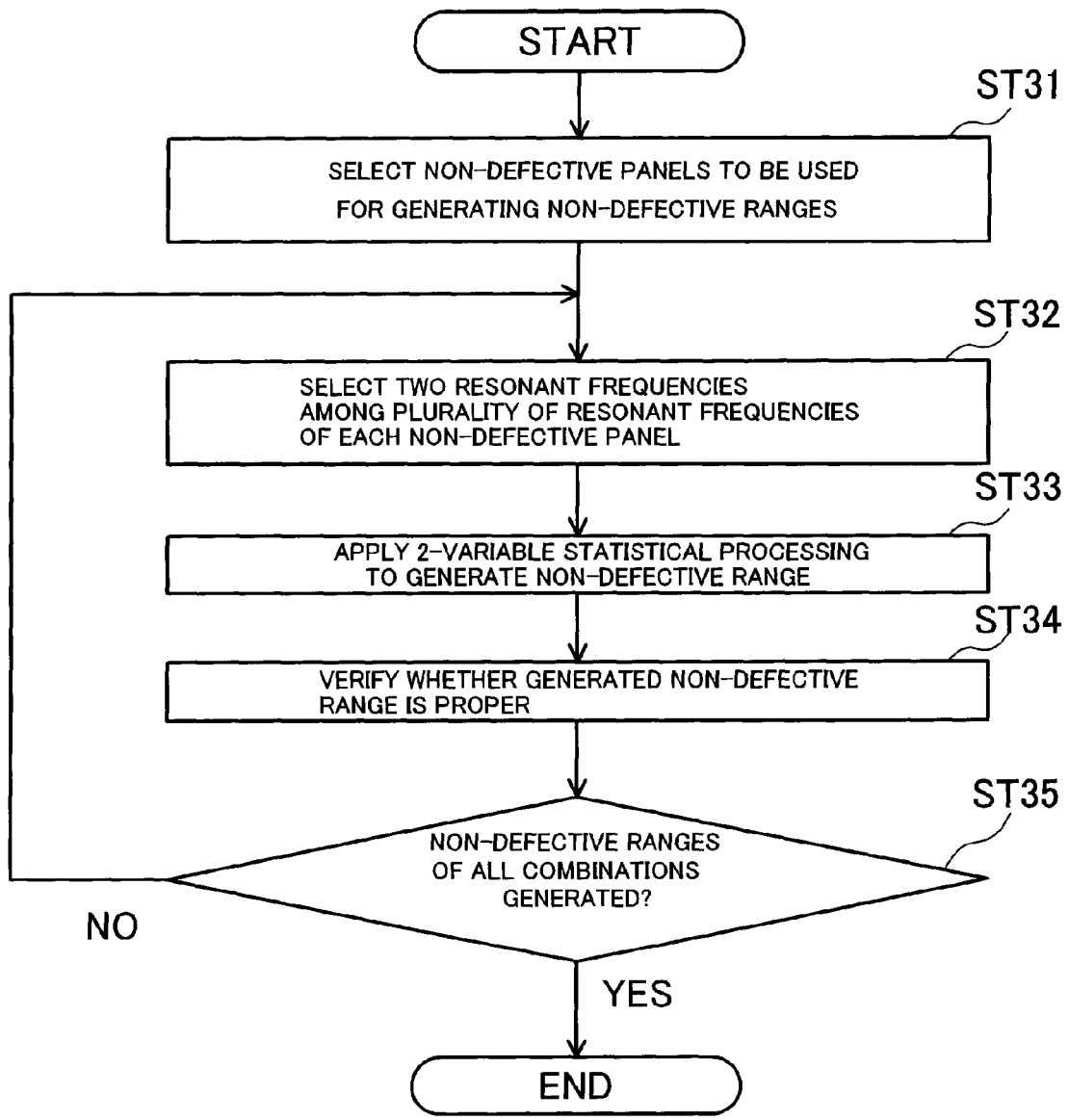
FIG. 12 is a flowchart showing steps for generating non-defective ranges.

FIG. 12 is a flowchart showing steps for generating non-defective ranges.

At Step ST31, non-defective panels are selected for generating non-defective ranges.

A Step ST32, among the plurality of resonant frequencies A, B, C, D . . . of the non-defective panels 1, 2, 3, 4 . . . extracted at the above-described Step ST22, a resonant frequency combination consisting of two resonant frequencies is selected.

At Step ST33, the set of one combination of resonant frequencies selected at the above-described Step ST32 is subjected to 2-variable statistical processing to generate a non-defective range on a coordinate system in which resonant frequencies are taken on coordinate axes.

Figure 13:
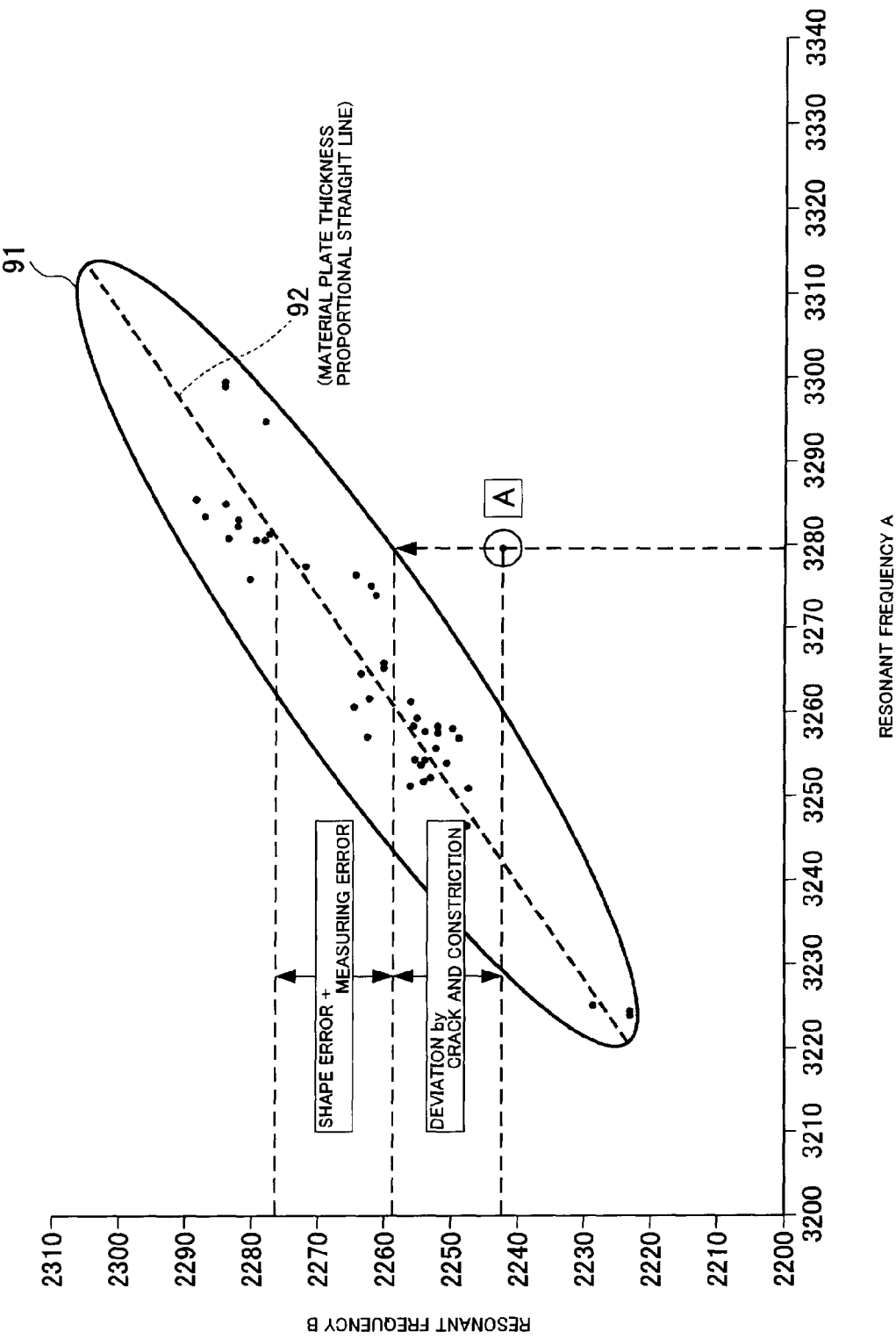
FIG. 13 is a diagram showing a non-defective range generated based on the results of statistical processing.

FIG. 13 is a diagram showing a non-defective range 91 generated based on the results of statistical processing. In FIG. 13, the horizontal axis and the vertical axis correspond to the combination of resonant frequencies (resonant frequencies A and B) selected at Step ST32.

Figure 14:
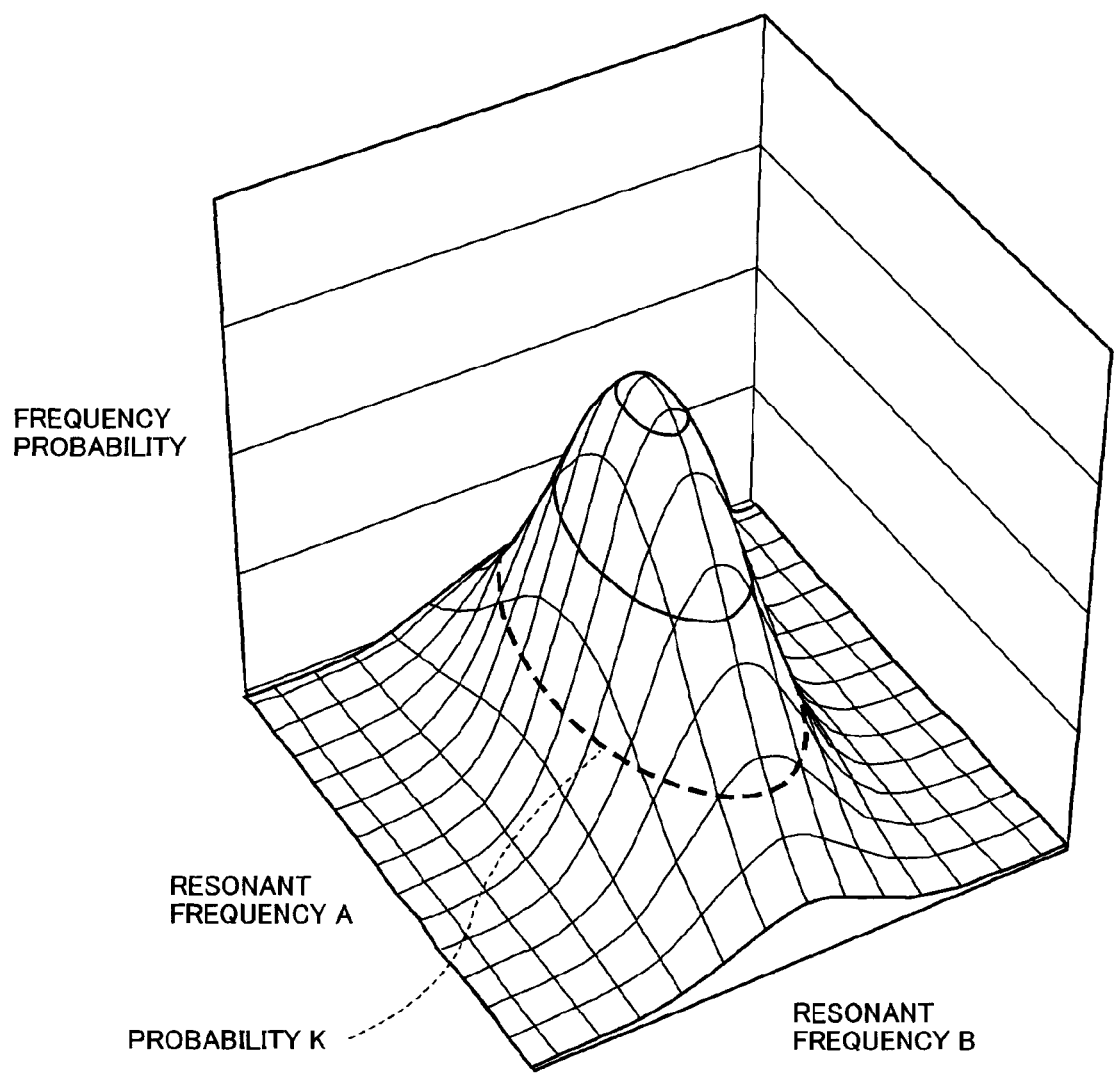
FIG. 14 is a two-dimensional regular distribution chart of resonant frequencies A and B.

At this step, averages $A_X$ and $A_Y$, standard deviations $S_X$ and $S_Y$, and a covariance $S_{XY}$ of these resonant frequencies A and B are calculated, and based on these averages and deviations, two-dimensional regular distributions by taking the resonant frequencies A and B on the coordinate axes as shown in FIG. 14 are obtained.

Next, from the two-dimensional regular distributions, an ellipse probability range of a predetermined probability K (0<K<1) is cut out and set as a non-defective range. Herein, the probability K is, for example, 98 percent.

More specifically, an elliptic non-defective range when the length of the longer axis of the probability ellipse is defined as $W_1$, the length of the shorter axis is defined as $W_2$, and the inclination of the longer axis is defined as T, is calculated by the following formula.

$$W_1 = \sqrt{L_1} \cdot \sqrt{-2\log(1.0 - K)}$$
$$W_2 = \sqrt{L_2} \cdot \sqrt{-2\log(1.0 - K)}$$
$$T = \arctan\left(-\frac{A}{B}\right)$$

[Numerical formula 1]

Herein, variables $L_1$, $L_2$, and A, B are calculated by the following formula.

$$L_1 = (S_X + S_Y + \sqrt{(S_X - S_Y)^2 + 4S_{XY}^2})/2$$ [Numerical formula 2]

$$L_2 = (S_X + S_Y - \sqrt{(S_X - S_Y)^2 + 4S_{XY}^2})/2$$

$$A = \sqrt{S_{XY}^2/((L_2 - S_X)^2 + S_{XY}^2)}$$

$$B = A(L_2 - S_X)/S_{XY}$$

As shown in FIG. 13, the resonant frequencies A and B positively correlate with each other. In other words, the inclination of the longer axis 92 of the ellipse of the non-defective range 91 is positive. The reason for this is described below.

The following formula shows the relationship between a resonant frequency f of a plate material and a plate thickness b of the plate material when the length of the plate material is defined as L, the Young's modulus of the plate material is defined as E, and the density of the plate material is defined as $\rho$.

$$f = \frac{\alpha^2}{2\pi L^2}\sqrt{\frac{E}{12\rho}} \cdot b$$ [Numerical formula 3]

As shown in the formula, the resonant frequency of the plate material is in proportion to the plate thickness.

Figure 15:
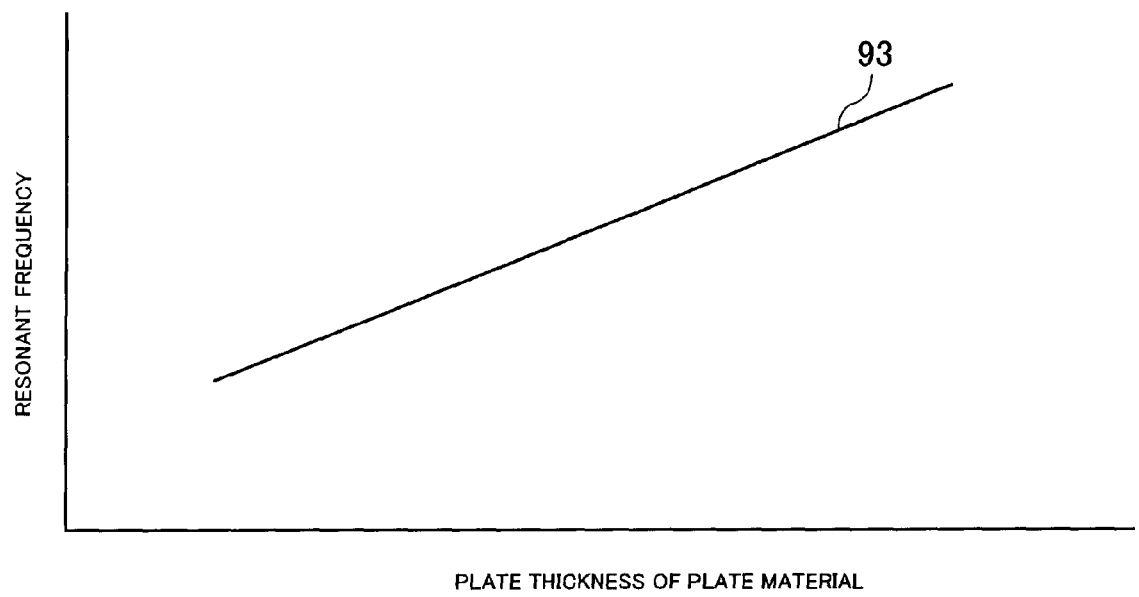
FIG. 15 is a diagram showing the relationship between the resonant frequency and the plate thickness of the plate material.

FIG. 15 is a diagram showing the relationship between the resonant frequency and the plate thickness of the plate material. In FIG. 15, the horizontal axis indicates the plate thickness of the plate material, and the vertical axis indicates the resonant frequency of the plate material.

As shown by the solid line 93 of FIG. 15, when the plate thickness of the plate material increases, the resonant frequencies inherent to the plate material also increase in proportion. In other words, unless the panel after being formed is constricted or cracked, the plate thickness of the formed panel is in proportion to the plate thickness of the plate material before being formed, so that the resonant frequencies of the non-defective panel which does not have constrictions and cracks are in proportion to the plate thickness of the plate material before formed.

Therefore, as shown in FIG. 13, a combination of resonant frequencies A and B positively correlate with each other. In other words, due to the variation in plate thickness of the plate materials of the non-defective panels, the resonant frequencies are distributed along a material plate thickness proportional straight line 92 with a positive inclination.

In actuality, as shown in FIG. 13, the resonant frequencies of the non-defective panels deviate from the material plate thickness proportional straight line 92 in the non-defective range, and it can be said that the deviation is derived from shapes and measuring errors. Thus, it can be said that a non-defective range generated by statistical-processing a set of a combination of resonant frequencies has a shape including variation in plate thickness of the plate materials to be used as materials.

As described in detail with reference to FIG. 6, the panel 10 has resonant frequencies different between the vibration propagation paths 16 and 17.

Therefore, for example, the resonant frequency A is defined as a resonant frequency associated with the vibration propagation path 16, and the resonant frequency B is defined as a resonant frequency associated with the vibration propagation path 17. Herein, it is assumed that the vibration propagation path 17 has a forming defective portion such as a constriction or crack.

When such resonant frequencies A and B of the panel 10 are measured and plotted on the coordinate system, due to an influence of the constriction or crack, the resonant frequencies are out of the non-defective range 91 as shown by the point A in FIG. 13. Herein, as described above, the forming defective portion is present on the vibration propagation path 17 associated with the resonant frequency B, so that the deviation of the point A from the non-defective range 91 appears as the deviation of the resonant frequency B. Thus, based on the generated non-defective range, it can be determined whether the quality of the panel is good.

Returning to FIG. 12, at Step ST34, it is verified whether the generated non-defective ranges are proper.

Figures 16A, 16B:
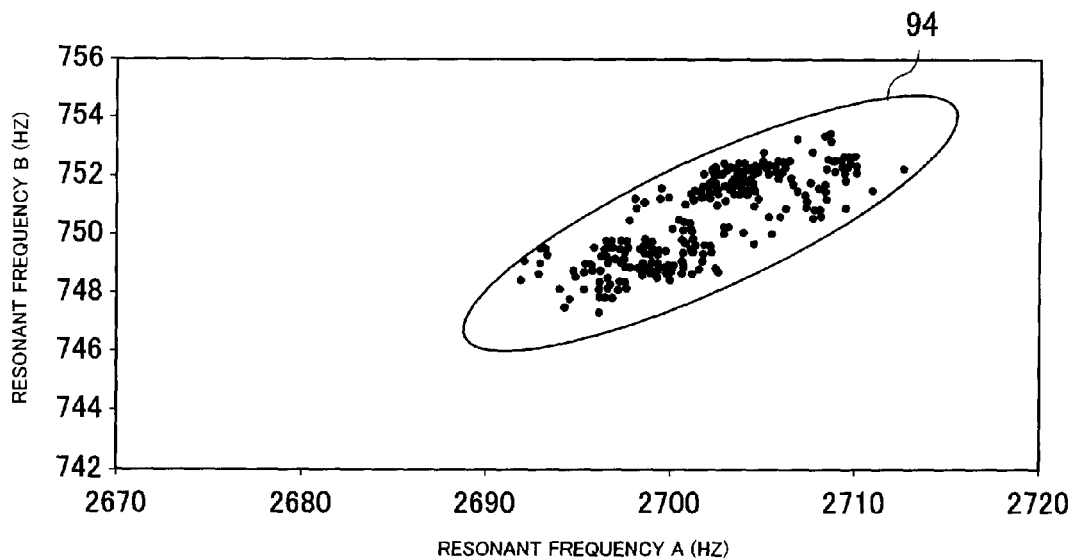
FIGS. 16($a$) and 16($b$) are diagrams showing an example of a non-defective range generated based on the results of statistical processing.
Figures 17A, 17B:
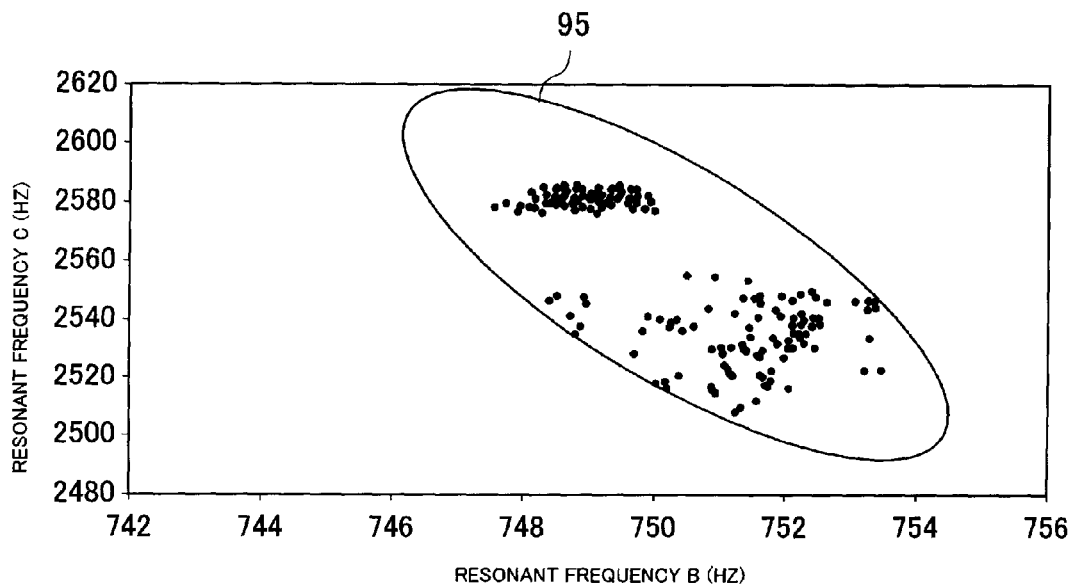
FIGS. 17($a$) and 17($b$) are diagrams showing an example of a non-defective range generated based on the results of statistical processing.

FIGS. 16(a) and 16(b) and FIGS. 17(a) and 17(b) are diagrams showing examples of non-defective ranges generated based on the results of statistical processing, respectively. More specifically, FIG. 16(a) shows values of the selected combination of resonant frequencies (resonant frequencies A and B) of non-defective panels, and FIG. 16(b) shows a non-defective range 94 generated as a result of statistical processing. FIG. 17(a) shows values of the selected combination of resonant frequencies (resonant frequencies B and C) of non-defective panels, and FIG. 17(b) shows a non-defective range 95 generated as a result of statistical processing.

As described above, the non-defective range generated by considering variation in plate thickness of the plate materials to be used as materials has positive correlation between the resonant frequencies. Therefore, at this step, a non-defective range which does not have a positive correlation is determined as improper and excluded. Accordingly, a non-defective range which does not have a positive correlation like the non-defective range 95 of FIG. 17 is excluded.

At this step, a non-defective range including a selected combination of resonant frequencies which were greatly influenced by disturbances is excluded. In detail, first, data of resonant frequencies included out of the generated non-defective range are eliminated, and then the above-described statistical processing is performed again to generate a non-defective range.

Figure 18A:
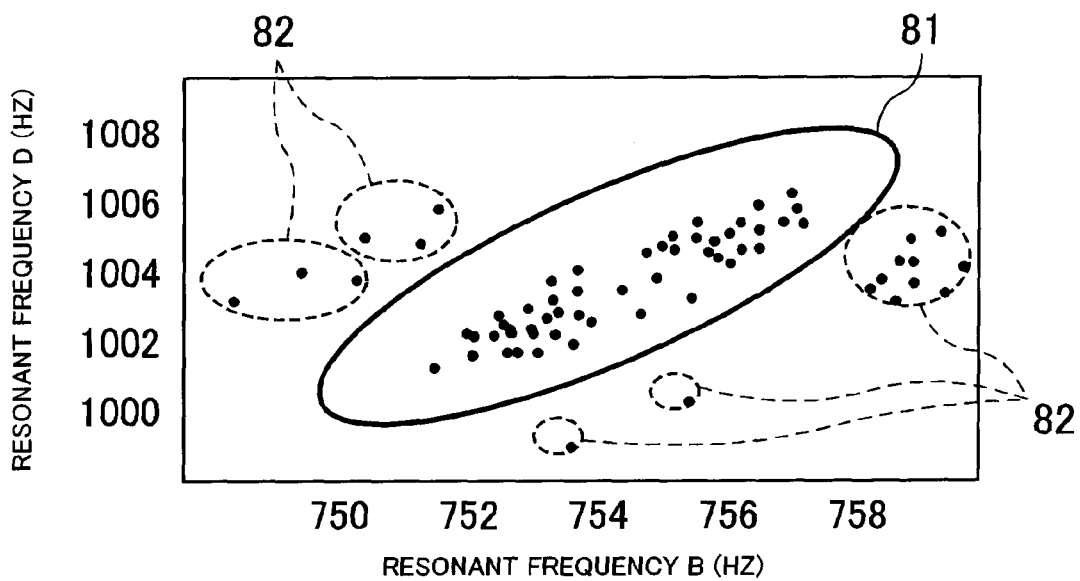
FIGS. 18($a$) and 18($b$) are diagrams showing an example of a non-defective range generated based on the results of statistical processing.
Figure 18B:
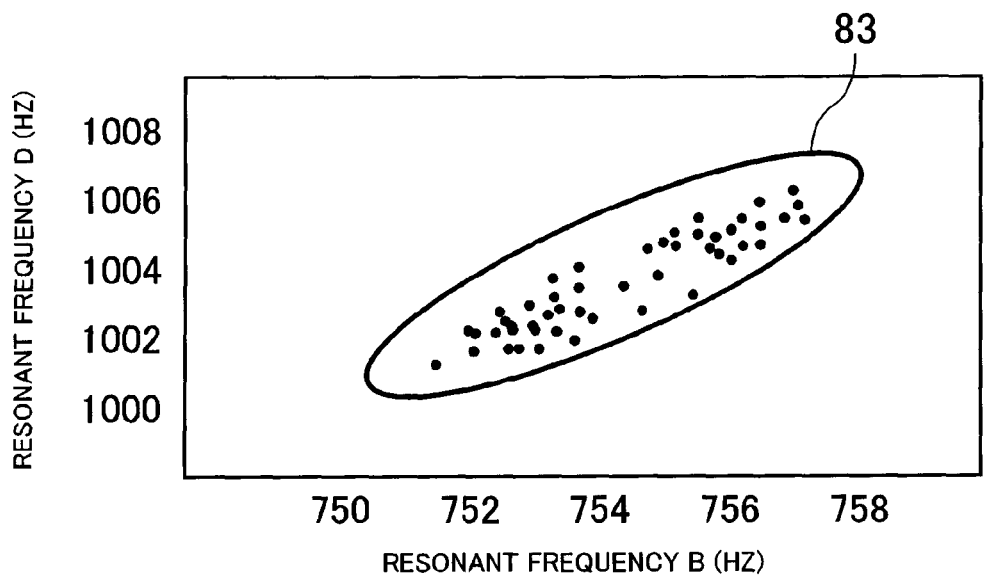

FIGS. 18(a) and 18(b) are diagrams showing examples of non-defective ranges generated based on the results of statistical processing. More specifically, FIG. 18(a) is a diagram showing an example including data of resonant frequencies out of the generated non-defective range 81, and FIG. 18(b) is a diagram showing an example of a regenerated non-defective range 83.

As shown by the dashed lines 82 in FIG. 18(a), due to influences of disturbances, the values of resonant frequencies scatter out of the non-defective range 81 in some cases. If a large amount of such data is included, this causes an erroneous determination, so that it is preferable that the data are excluded. Therefore, upon eliminating the data of resonant frequencies out of the non-defective range 81 as disturbances, the non-defective range 83 as shown in FIG. 18(b) is regenerated.

Next, by dividing the number of works in the regenerated non-defective range by the number of works in the non-defective range before being regenerated, the following inspection value is calculated.

Inspection value=number of works in regenerated non-defective range/number of works in non-defective range before being regenerated Next, it is determined whether the calculated inspection value is not more than a predetermined threshold (for example, 98%), and a non-defective range whose inspection value is not more than the predetermined threshold is determined as being greatly influenced by disturbances and excluded. Accordingly, the determination accuracy can be further improved.

Returning to FIG. 12, at Step ST35, it is determined whether non-defective ranges of all combinations have been generated. When it is determined as "YES," the processing for generating the non-defective ranges is ended, and when it is determined as "NO," the process shifts to Step ST32.

Next, steps for executing the inspection of the panel to be inspected (Step ST7 in FIG. 2) will be described with reference to FIG. 19 and FIG. 20.

FIG. 19 is a flowchart showing steps for executing the inspection of the panel to be inspected.

At Step ST41, one non-defective range is selected among a plurality of non-defective ranges generated at the above-described Step ST4.

At Step ST42, the selected non-defective range and resonant frequencies of the panel to be inspected are compared and a probability distance is calculated.

Figure 20:
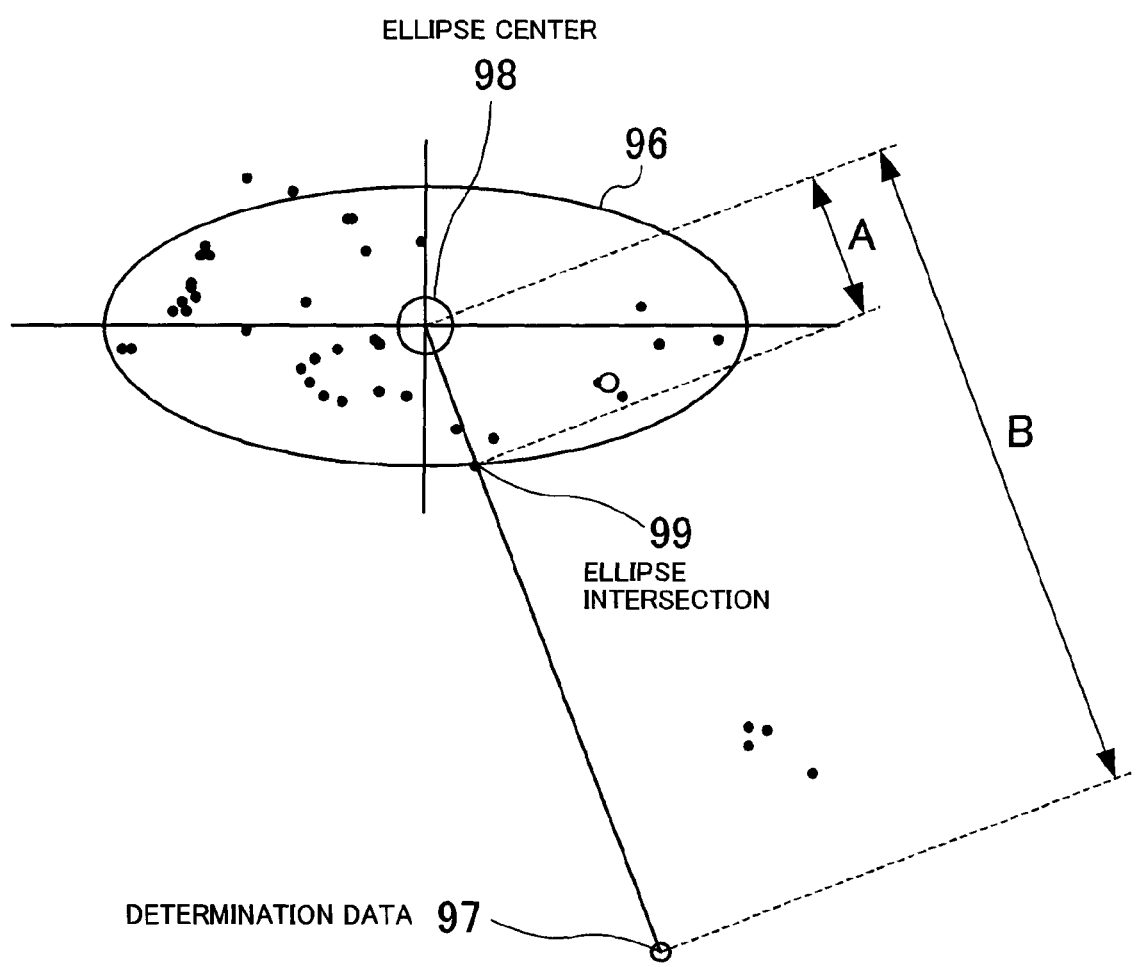
FIG. 20 is a chart on which resonant frequencies of the panel to be inspected are plotted as determination data on a non-defective range.

FIG. 20 is a diagram showing resonant frequencies of the panel to be inspected extracted at Steps ST5 and ST6, plotted as determination data 97 on the selected non-defective range 96.

At this step, an ellipse center 98 of the selected non-defective range 96 and the determination data 97 are connected by a straight line, and the distance from the ellipse center 98 to an ellipse intersection 99 is defined as A, and the distance from the ellipse center 98 to the determination data 97 is defined as B.

Next, the probability distance=B/A is defined and this probability distance is calculated. Herein, when the probability distance is not more than 1, that is, when the determination data 97 is included in the non-defective range 96, this probability distance is set to 1.

At Step ST43, it is determined whether probability distances of the panel to be inspected in all non-defective ranges have been calculated. When it is determined as "YES," the process shifts to Step ST44, and when it is "NO," the process shifts to Step ST41.

At Step ST44, based on the calculated probability distances of the panel to be inspected in all non-defective ranges, a determination value which is an index for determining the quality of the panel to be inspected is calculated, and then it is determined whether the quality of the panel to be inspected is good.

More specifically, at this step, as in the following formula, by multiplying the probability distances ($B_1/A_1$, $B_2/A_2$, $B_3/A_3$ ...) of the panel to be inspected in all non-defective ranges, the determination value is calculated.

$$\text{Determination value} = \frac{B_1}{A_1} \times \frac{B_2}{A_2} \times \frac{B_3}{A_3} \times \ldots \quad \text{[Numerical formula 4]}$$

Next, by determining whether this determination value is smaller than a predetermined set value, it is determined whether the panel to be inspected is non-defective. Herein, the set value is an arbitrary value not less than 1 (one). Thus, by determining the quality of the panel to be inspected based on a plurality of probability distances calculated from a plurality of non-defective ranges, the probability of erroneous determination can be reduced.

The panel inspection apparatus 1 of the present exemplary embodiment brings about the following operation and effect.

(1) Among a plurality of non-defective panels determined as non-defective in advance, combinations of resonant frequencies unique to the non-defective panels are selected, and a set of the combinations of resonant frequencies are subjected to 2-variable statistical processing to generate non-defective ranges on coordinate systems in which the resonant frequencies are taken on the coordinate axes. Next, from the panel to be inspected, combinations of resonant frequencies unique to the panel to be inspected are selected, and the combinations of resonant frequencies and the generated non-defective ranges are compared to determine whether the quality of the panel is good.

Herein, particularly, by selecting two or more resonant frequencies with different vibration propagation paths as the combination of resonant frequencies, a non-defective range having an extent in which variation in plate thickness of the plate materials to be used as materials is considered can be generated. Based on this non-defective range, by determining whether the quality of the panel to be inspected is good, the quality of the panel can be inspected by considering the variation in plate thickness of the materials.

As described above, it is important to select two or more resonant frequencies with different vibration propagation paths. Therefore, by measuring vibrations at different positions by using two or more sensors, vibrations of different propagation paths can be reliably measured. In this case, when generating a non-defective range by frequency-converting the oscillatory waveforms and statistically processing the resonant frequencies which can be stably extracted, by combining the resonant frequencies obtained by the sensors, a non-defective range can be generated.

By detecting vibrations of a panel by the vibration sensors while vibrating the panel by the vibrator, the quality of the panel can be inspected in a short time. Accordingly, for example, the panel inspection apparatus 1 can be incorporated in a panel production line.

(2) When determining whether the quality of the panel to be inspected is good, by using only non-defective ranges having a positive correlation between resonant frequencies, erroneous determination on the quality of the panel can be prevented.

MODIFIED EXAMPLE

A modified example of the panel inspection apparatus 1 of the above-described embodiment will be described. As described above, the panel inspection apparatus 1 of the above-described embodiment can perform inspection in a short time, so that the panel inspection apparatus 1 can be incorporated in an existing press-formed panel production line without major modification.

Figure 21:
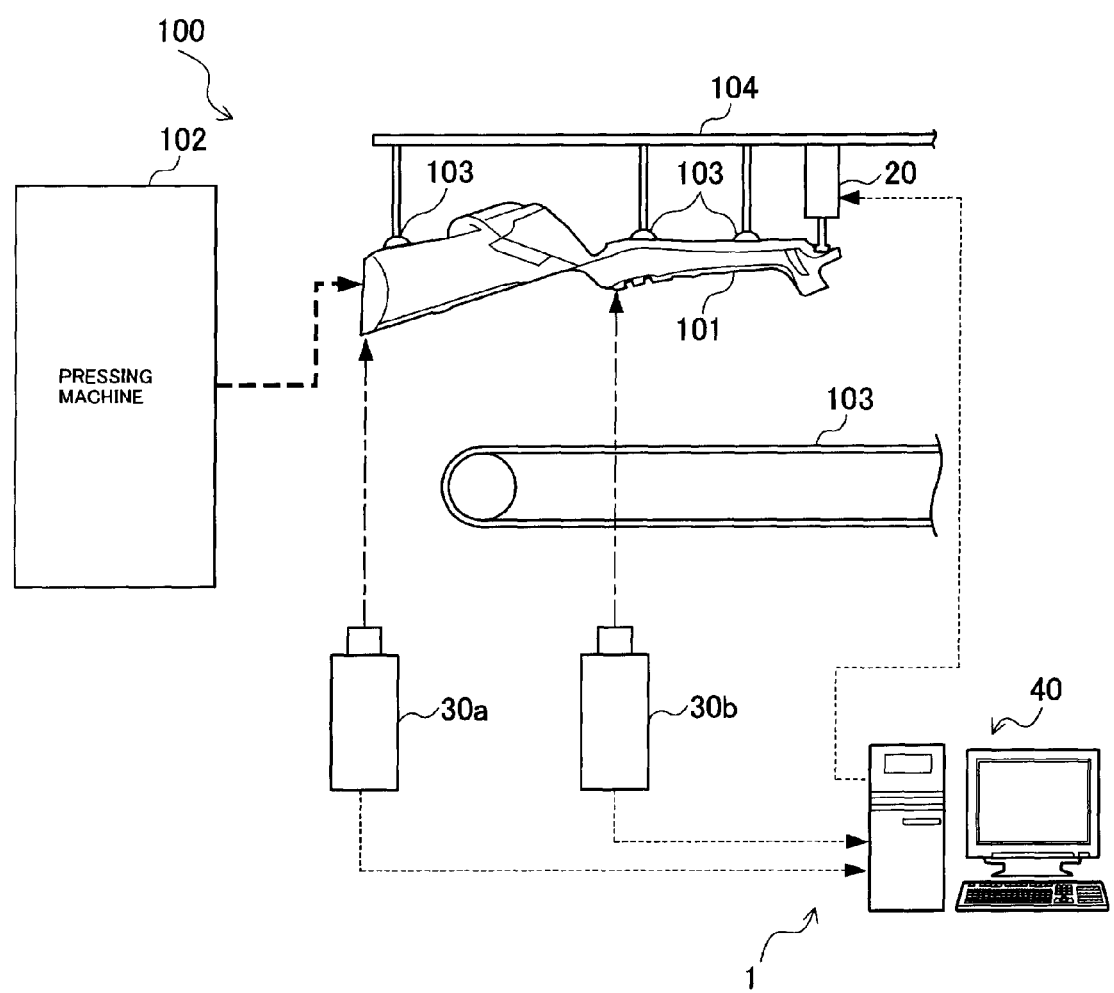
FIG. 21 is a side view showing a construction of a press-formed panel production line including the panel inspection apparatus of the above-described embodiment.

FIG. 21 is a side view showing a construction of a press-formed panel production line 100 in which the panel inspection apparatus 1 is incorporated.

The production line 100 includes a pressing machine 102 for forming a panel 101 and a band-like conveyor 103 which conveys the panel 101 to the next process.

In this production line 100, the panel inspection apparatus 1 is provided by using an extra space of the conveyor 103.

More specifically, the vibrator 20 of the panel inspection apparatus 1 is attached to a handling 104 which holds the panel 101 formed by the pressing machine 102. Two vibration sensors 30a and 30b of the panel inspection apparatus 1 are installed below the conveyor 103 and detect vibrations of the panel 101 through gaps of the conveyor 103.

Thus, by attaching the vibrator 20 to the handling 104 and detecting vibrations by the vibration sensors 30a and 30b through gaps of the conveyor 103, the quality of the panel 101 can be inspected while conveying the panel 101. Accordingly, the cycle time required for inspecting the panel 101 can be shortened.

The handling 104 has a plurality of vacuum cups 105 made of elastic materials such as rubber or urethane, and by adsorbing the panel 101 to the vacuum cups 105, the panel 101 is held.

By using such vacuum cups 105, vibrations, etc., caused by moving the handling 104 other than vibrations caused by the vibrator 20 can be prevented from being transmitted to the panel 101. By using the vacuum cups 105, the panel 101 can be stably held regardless of the shape thereof. Particularly, the panel 101 press-formed by the pressing machine 102 may be warped, however, even when such warping occurs, the panel 101 can be reliably held.

Figure 22:
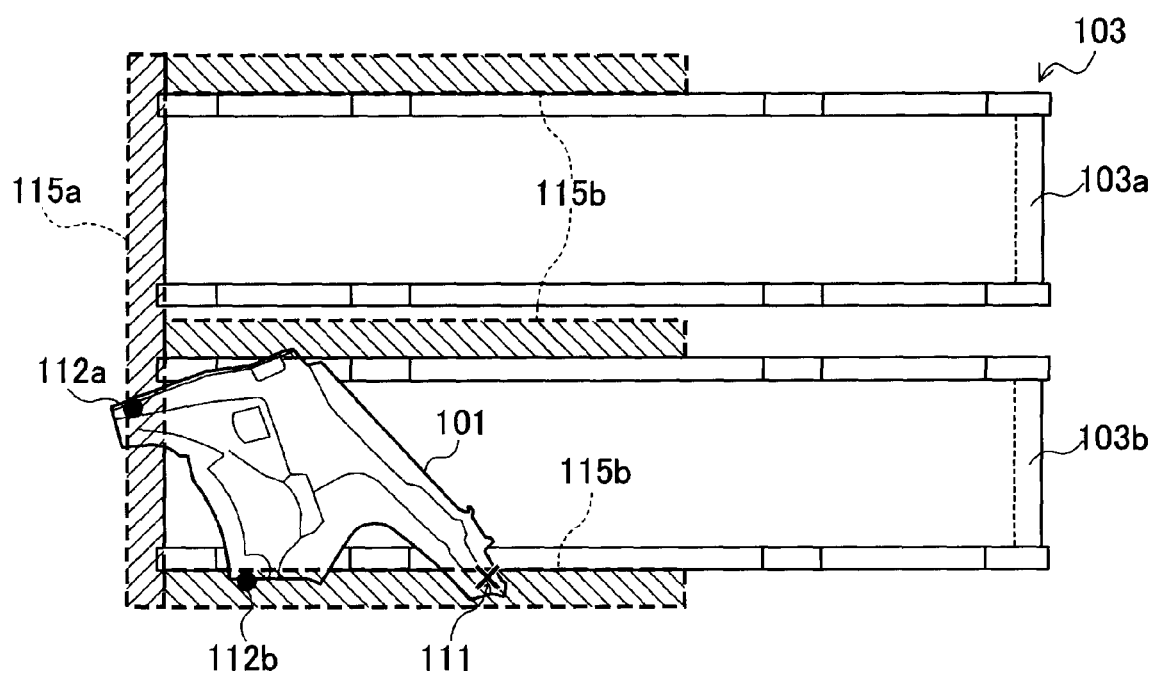
FIG. 22 is a top view showing a construction of a press-formed panel production line including the panel inspection apparatus of the above-described embodiment.

FIG. 22 is a top view showing a construction of the press-formed panel production line 100 in which the panel inspection apparatus 1 is incorporated.

As shown in FIG. 22, by dividedly providing the conveyors 103a and 103b, a region 115a in which vibrations of the panel 101 can be detected by the vibration sensor 30a and regions 115b in which the vibrations of the panel 101 can be detected by the vibration sensor 30b can be secured. Accordingly, vibrations of the panel 101 at the detection positions 112a and 112b can be detected by the vibration sensors 30a and 30b while vibrating the vibration position 111 by the vibrator 20.

In addition, by detecting the vibrations of the panel 101 at the detection positions 112a and 112b positioned at end portions of the panel 101, vibrations which were less influenced by noise can be detected. The reason for this is that at end portions as open ends of the panel 101, the phases of vibrations of the panel 101 coincide with each other and the vibration intensity increases.

Next, an influence of vibrations caused by conveyance on inspection of the quality will be described with reference to FIG. 23.

Figure 23:
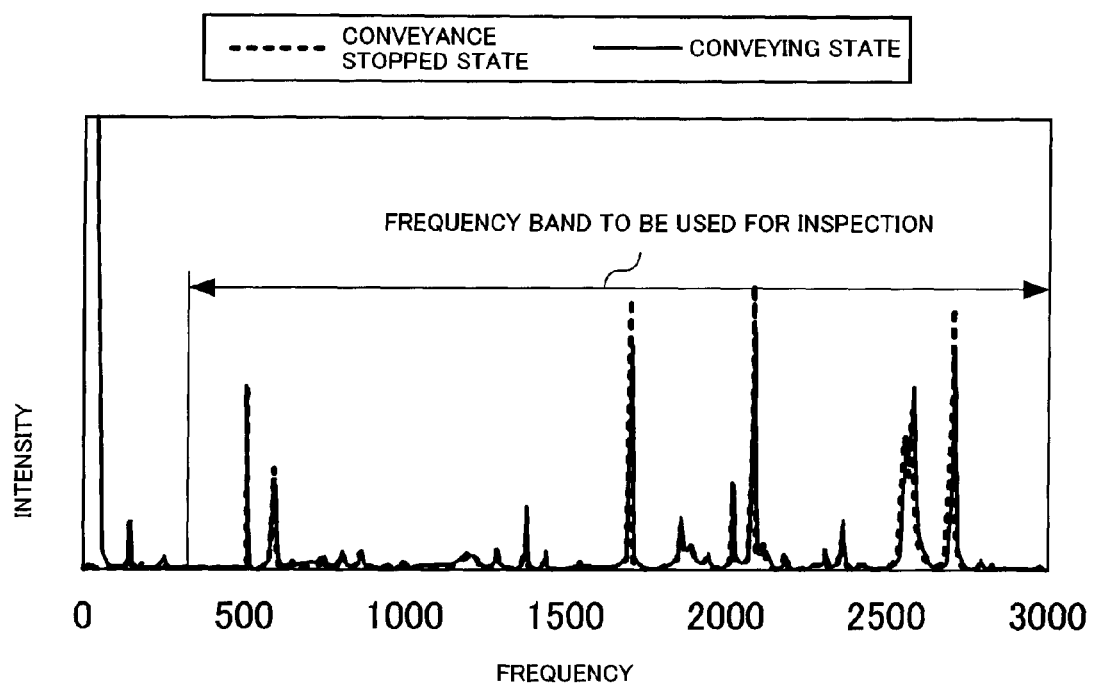
FIG. 23 is a diagram showing a waveform of frequency components of vibrations of the panel.
Figure 24:
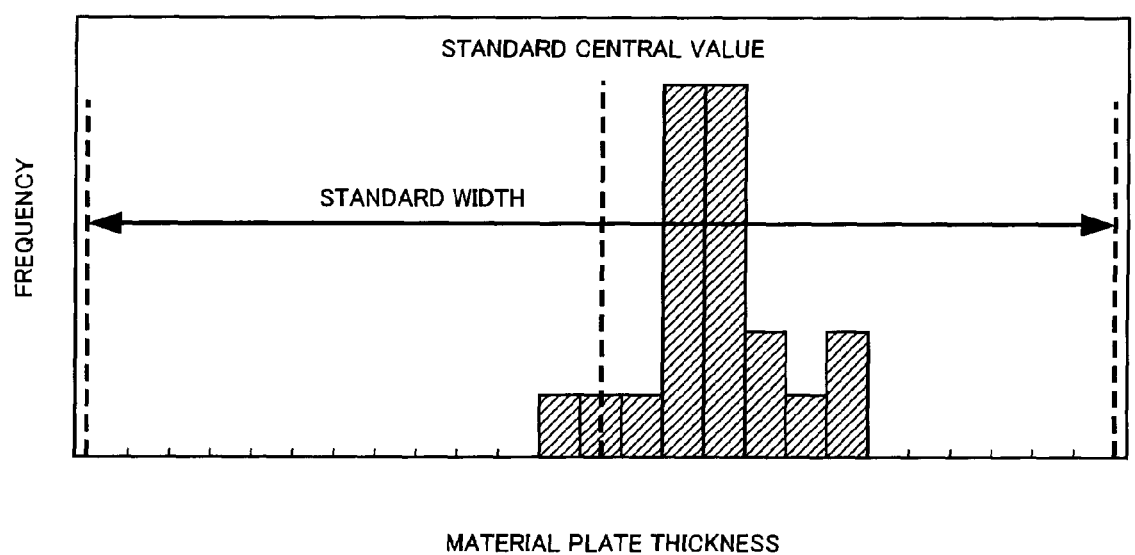
FIG. 24 is a histogram showing variation in plate thickness of a plurality of steel plates included in one standard.

FIG. 23 is a diagram showing a waveform of frequency components of the vibrations of the panel. In detail, the dashed line in FIG. 23 shows a waveform of frequency components of the vibrations of the panel measured by stopping conveyance, and the solid line in FIG. 23 shows a waveform of frequency components of the vibrations of the panel measured while conveying it.

As shown in FIG. 23, the waveform is greatly different only in the region not more than about 200 Hz between the case where the vibrations of the entire panel stop after the time sufficiently elapses since the stop of conveyance, and in the case where the vibrations stop immediately after the conveyance is stopped. In other words, the frequency band of the vibrations caused by conveyance is between several Hz and about 200 Hz, and is different from the frequency band of the vibrations caused by the vibrator. Therefore, when extracting resonant frequencies of the panel, a low frequency band of not more than about 200 Hz is cut off, and only the high frequency band is used for the inspection, and accordingly, the quality of the panel can be inspected without influences of vibrations caused by conveyance.

The production line 100 of this modified example in which the panel inspection apparatus 1 of the above-described embodiment is incorporated brings about the following effect in addition to the same effect as in the above-described embodiment.

(3) By incorporating the panel inspection apparatus 1 in the press-formed panel production line 100, the time cycles of the panel production and the panel inspection can be shortened.

While description has been made in connection with specific embodiments and modified examples of the present invention, it will be obvious to those skilled in the art that various changes and modification may be made therein without departing from the present invention. It is aimed, therefore, to cover in the appended claims all such changes and modifications falling within the true spirit and scope of the present invention.

DESCRIPTION OF REFERENCE NUMERALS AND SIGNS 1 panel inspection apparatus
20 vibrator (vibrator)
30 vibration sensor (vibration detector)
40 control device
100 production line

What is claimed is:

1. A panel inspection apparatus that determines whether a quality of a panel to be inspected is good based on resonant frequencies obtained by vibrating panels determined as non-defective in advance, the panel inspection apparatus comprising:
a vibrator that vibrates the panel;
a vibration detector that detects vibrations of the panel;
a resonant frequency extracting unit for extracting a plurality of resonant frequencies of the panel to be inspected by using the vibrator and the vibration detector;
a resonant frequency selecting unit that selects one or more combinations of resonant frequencies consisting of two or more resonant frequencies with different vibration propagation paths among the plurality of resonant frequencies extracted by the resonant frequency extracting unit;
a non-defective range generating unit for generating non-defective ranges related to a plurality of non-defective panels determined as non-defective in advance on coordinate systems in which the resonant frequencies are taken on coordinate axes by executing the resonant frequency extracting unit and the resonant frequency selecting unit and statistically processing a set of the combinations of resonant frequencies selected for each non-defective panel; and
a panel quality determining unit for determining whether the quality of the panel to be inspected is good based on comparison between combinations of resonance frequencies selected for the panel to be inspected and the non-defective ranges generated by the non-defective range generating unit upon executing the resonant frequency extracting unit and the resonant frequency selecting unit for the panel to be inspected.

2. The panel inspection apparatus according to claim 1, wherein the panel quality determining unit uses only non-defective ranges which have a positive correlation between resonant frequencies among the non-defective ranges generated by the non-defective range generating unit for determining whether the quality of the panel to be inspected is good.

3. The panel inspection apparatus according to claim 1, wherein the panel inspection apparatus is incorporated in a press-formed panel production line consisting of a plurality of processes.

4. A panel inspection method for determining whether a quality of a panel to be inspected is good based on resonant frequencies obtained by vibrating panels determined as non-defective in advance, the method comprising:

a resonant frequency extracting step including vibrating the panel, detecting vibrations of the panel, and extracting a plurality of resonant frequencies of the panel are extracted;

a resonant frequency selecting step including selecting one or more combinations of resonant frequencies consisting of two or more resonant frequencies with different vibration propagation paths, among the plurality of resonant frequencies extracted at the resonant frequency extracting step;

a non-defective range generating step including executing the inspection step for a plurality of non-defective panels determined as non-defective in advance, and statistically processing a set of the combinations of the resonant frequencies selected for the non-defective panels, and generating non-defective ranges on coordinate systems in which the resonant frequencies are taken on coordinate axes; and a panel quality determining step including executing the inspection step for the panel to be inspected, comparing combinations of resonant frequencies selected for the panel to be inspected and the non-defective ranges generated by a non-defective range generating unit, and determining whether the quality of the panel to be inspected is good based on a comparison.

5. The panel inspection method according to claim 4, further comprising:

using only non-defective ranges which have a positive correlation between resonant frequencies among the non-defective ranges generated by the non-defective range generating unit for determining whether the quality of the panel to be inspected is good.

* * * * *